United States Patent [19]
Follen et al.

[11] Patent Number: 6,166,079
[45] Date of Patent: *Dec. 26, 2000

[54] DFMO FOR THE TREATMENT OR PREVENTION OF CERVICAL INTRAEPITHELIAL NEOPLASIA

[75] Inventors: Michele Follen; Wuan K. Hong, both of Houston; Reuben Lotan, Kingwood; Walter Hittelman; Kenji Nishioka, both of Houston, all of Tex.

[73] Assignee: Board of Regents, The University of Texas System, Austin, Tex.

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/777,773

[22] Filed: Dec. 30, 1996

Related U.S. Application Data

[63] Continuation-in-part of application No. 08/719,913, Sep. 25, 1996, abandoned.

[51] Int. Cl.⁷ .................................................. A61K 31/195
[52] U.S. Cl. ............................................................ 514/564
[58] Field of Search ............................................. 514/564

[56] References Cited

FOREIGN PATENT DOCUMENTS 0 162 413  11/1985  European Pat. Off. .

OTHER PUBLICATIONS

Mitchell, et al., "Decreased PCNA Expression in Cervical Premalignant Lesions After Chemoprevention by α–Difluoromethylornithine (DFMO)," *Proc. Annu. Meet. Am. Assoc. Cancer Res.*, 37:185, Mar. 1996.

Kelloff, et al., "Strategies for Phase II Cancer Chemoprevention Trials: Cervis, Endometrium and Ovary," *J. Cell. Biochem. Suppl.*, 23:1–9, 1995.

Moon, et al., "Chemoprevention of OH–BBN–Induced Bladder Cancer in Mice by Oltipraz, Alone and in Combination with 4–HPR and DFMO," *Anticancer Research*, 14(1a):5–11, 1994.

Moon, et al., "Chemoprevention of OH–BBN–Induced Bladder Cancer in Mice by Piroxicam," *Carcinogensis*, 14:1487–1489, 1993.

Mitchell, et al., "The Natural History of Cervical Intraepithelial Neolasia: An Argument fo Intermediate Endpoint Biomarkers," *Cancer Epidemiology, Biomarkers & Prevention*, 3:619–626, Oct./Nov. 1994.

"Infection Management, The Risk for Cervical Disease in HIV–Infected Women," A Report from the CDC on Four Studies in New York City, *Primary Care & Cancer*, Oct. 1991.

Creaven, et al., "Evaluation of α–Difluoromethylornithine as a Potential Chemopreventive Agent: Tolerance to Daily Oral Administration in Humans," *Cancer Epidemiology, Biomarkers & Prevention*, 2:243–247, May/Jun. 1993.

Griffin, et al., "Phase I Trial and Pharmacokinetic Study of Intravenous and Oral α–Difluoromethylornithine," *Investigational New Drugs*, 5:177–186, 1987.

Carbone, et al., "Phase I and Pharmacokinetics Study of Difluoromethylornithine (DFMO), a Potential Chemopreventive," Proceedings of the American Association for Cancer Research, vol. 32, Mar. 1991.

Croghan, et al., Dose–Related α–Difluoromethylornithine Ototxicity, *Am. J. Clin Oncol CCT*) 14(4):331–335, 1991.

Griffin, et al., "Phase I Trial & Pharmacokinetic Study of IV & High Dose Oral α–Difluoromethylornithine (DFMO)," Proceedings of the American Society of Clinical Oncology Twentieth Annual Meeting, May 6–8, Toronto, Ontario, Canada, 1984.

Horn, et al., "Phase I–II Clinical Trial with Alpha–Difluoromethylornitine—An Inhibitor of Polyamine Biosynthesis," *Eur. J. Cancer Clin Oncol.*, 23(8):1103–1107, 1987.

Kelloff, et al., "Surrogate Endpoint Biomarkers for Phase I Cancer Chemoprevention Trials," *Journal of Cellular Biochemistry, Supplement*, 19:1–9, 1994.

Kuman, et al., "Interim Guidelines for Management of Abnormal Cervical Cytology," *JAMA*, 271(23):1866–1869, Jun. 1994.

Mamont, et al., "Anti–Proliferative Properties of DL–α–Difluoromethylornithine in Cultured Cells A Consequence of he Irreversible Inhibition of Ornithine Decarboxylase," *Biochemical and Biophysical Research Communucations*, 81(1):58–66, Mar. 1978.

Meyskens, Jr., et al., "Enhancement of Regression of Cervical Intraepithlial Neoplasia I (Moderate Dysplasia) with Topically Applied All–trans–Retinoic Acid: A Randomized Trial," *Journal of the National Cancer Institute*, 86(7):539–543, Apr. 1994.

Wagner, et al., "Resolution of the Enantiomers of Varous α–Substituted Ornithne and Lysine Analogs by High–Performance Liquid Chromatography with Chiral Eluant and by Gas Chromatography on Chirasil–Val," *Analytical Biochemistry*, 164:102–116, 1987.

Creaven, et al., "Phase I Study of Difluoromethylornithine (DFMO) as a Chemopreventive Agent," Proceedings of ASCO, vol. 11, Mar. 1992.

Love, et al., "Randomized Phse I Chemoprevention Dose–Seeking Study of α–Difluoromethylornithine," *Journal of the National Cancer Institute*, 85(9):732–737, May 1993.

(List continued on next page.)

*Primary Examiner*—William R. A. Jarvis
*Attorney, Agent, or Firm*—Fulbright & Jaworski, LLP

[57] ABSTRACT

Methods for treating, preventing, controlling the growth of and/or reducing the risk of developing cervical cancer, particularly in patients with cervical intraepithelial neoplasia are provided employing pharmaceutically acceptable preparations of DFMO. Methods for treating a patient having cervical intraepithelial neoplasia, which methods comprise administering DFMO alone or in combination with a cytotoxic or cytostatic agent, are also provided.

19 Claims, 6 Drawing Sheets

OTHER PUBLICATIONS

Garewal, et al., "Low Dose Difluoromethylornithine (DFMO) Produces Significant Changes in Polyamine Content of Upper GI Mucosa in Patients with Barrett's Esophagus," Digestive Disease Week and the 92$^{nd}$ Annual Meeting of The American Gastroenterological Assocation, New Orleans, LA, May 19–22, 1991.

Nishioka, et al., "Polyamines as Biomarkers of Cervical Intraepithelial Neoplasia," *Journal of Cellular Biochemistry, Supplement*, 23:87–95, 1995.

Pendyala, et al., "Urinary and Erythrocyte Polyamines During the Evaluation of Oral α–Difluoromethylornithine in a Phase I Chemoprevention Clinical Trial," *Cancer Epidemiology, Biomarkers & Prevention*, 2:235–241, May/Jun., 1993.

Crowell, et al., "Chronic Toxicity Studies of the Potential Cancer Preventive 2–(Difluoromethyl)–dl–Ornithine," *Fundamental and Applied Toxicology*, 22:341–354, 1994.

Mitchell, et al., "Chemoprevention Trials and Surrogate End Point Biomarkers in the Cervix," *Cancer Supplement*, 76(10)1956–1977, Nov. 1995.

Mitchell, et al., "Chemoprevention Trials in the Cervix: Design, Feasibiliy, and Recruitment," *Journal of Cellular Biochemistry, Supplement*, 23:104–1112, 1995.

Search Report, Aug. 6, 1996.

Search Report, Aug. 9, 1996.

DFMO FOR THE TREATMENT OR PREVENTION OF CERVICAL INTRAEPITHELIAL NEOPLASIA

The present application is a continued prosecution application (CPA) of U.S. Ser. No. 08/777,773 filed Dec. 30, 1996; U.S. Ser. No. 08/777,773 is a continuation-in-part application of U.S. Ser. No. 08/719,913 filed Sep. 25, 1996 now abandoned.

The government owns rights in the present invention pursuant to contract number CN01-2 5433-02 N01-CN-25433-02 from the National Cancer Institute.

FIELD OF THE INVENTION

The present invention provides a pharmaceutical formulation and a method for its use in the prevention of cervical cancer. More specifically, the present invention provides a composition comprising alpha-difluoromethylornithine for treating, preventing, reducing the risk of and/or controlling the growth and progression of cervical intraepithelial neoplasia grade III into malignancy.

BACKGROUND OF THE INVENTION AND DESCRIPTION OF THE PRIOR ART

Despite the advent of the Papanicolaou (Pap) smear, cervical cancers and pre-cancers remain important health problems for women, especially underobserved women in the United States (U.S.) and women in underdeveloped countries (Parkin, 1993). The incidence of both invasive cervical cancer and carcinoma-in-situ are increasing in the U.S. The reasons for this increase are unknown. In the U.S., an estimated 2,500,000 women will have abnormal Pap smears demonstrating atypical cells of uncertain significance and low-grade intraepithelial lesions (lesions of HPV and CIN 1) annually (Kurman, 1994). The exact number of patients with high-grade squamous intraepithelial lesions (CIN II and III), not classified as carcinoma-in-situ, is unknown.

A risk factor for cervical cancer is HPV. The most common types of HPV are those classified as high risk (HPV 16, 18, 45, and 56), intermediate risk (HPV 31, 33, 35, 51, 52, and 58), and low risk (HPV 6, 11). The high and intermediate risk types have been identified in 77% of high grade cervical intraepithelial neoplasia (CIN) and squamous intraepithelial lesions (SIL) and in 84% of invasive lesions. Cohort studies demonstrate that women with HPV infection have 11–60 times increased risk of developing high grade CIN and 15–50 times increased risk of developing invasive cancer than do women without HPV infection for which the high-risk HPV types include types 16, 18, 45, and 56. This association has been consistent and independent of the HPV assay method employed or epidemiologic study design (Bosch, 1995).

Chemoprevention is the use of chemical agents (micro-nutrients, pharmaceuticals) to prevent or delay the development of cancer in healthy populations (Kelloff, 1994; Daly, 1993). These agents, which block the initiating and promoting events of carcinogenesis, augment the preventive strategy, which includes the avoidance of carcinogens in the environment (referred to as primary prevention) and participation in screening programs (referred to as secondary prevention), hence serving as a tertiary preventative measure.

Because most current chemopreventive agents can cause side effects, they are used in individuals who have higher risk of developing cancer (for example, those with premalignant lesions). Intervention in the precancerous stage may prevent a lesion from becoming invasive (Spom, 1993). The advantage of chemoprevention in the treatment of a pre-neoplastic condition is that the effects of chemoprevention are systemic, thus pre-neoplastic cells in all areas of the body are treated. Chemoprevention studies use surrogate endpoint biomarkers (SEB's) as intermediate measures of cancer development. These markers should be differentially expressed in normal and high-risk tissue, be measured with acceptable sensitivity and specificity, and be modulated by the chemopreventive under study. SEB's provide a glimpse of cancer biology and its modulation (Boone, 1990).

There are several reasons why chemoprevention is attractive for cervical lesions. These reasons reflect the belief that pre-cancers, like cancers, represent a systemic process. Many colposcopy patients smoke, and many of these patients also have preneoplastic and neoplastic lesions of the aerodigestive tract. Infection with HPV affects the entire squamous epithelium of the female genital tract, and up to 40% of patients with CIN have multifocal lesions of the vagina, vulva, and perianal area.

Polyamines (putrescine, spermidine, and spermine) and their precursors (arginine and ornithine) are thought to play critical roles in cellular maintenance, proliferation, differentiation, and transformation; thus polyamines might be considered surrogate endpoint biomarkers of carcinogenesis. Polyamines are differentially expressed in normal and high-risk tissue; measured with acceptable sensitivity and specificity; and can be modulated by DFMO. Polyamines and their precursors can be measured in tissue, red blood cells, plasma, and urine. Ornithine Decarboxylase (ODC), a key enzyme in polyamine biosynthesis, is considered a proto-oncogene that is crucial for the regulation of cellular growth and transformation and is irreversibly inhibited by the drug α-difluoromethylornithine (DFMO). DFMO is considered a potent anti-proliferative chemopreventive agent and has been studied in other organ sites but has not previously been studied in the cervix (Verma, 1987; Auvinen, 1992).

ODC catalyzes the first step in the biosynthesis of putrescine (a diamine), spermidine and spermine, the three major polyamines of mammalian cells. In vitro studies show that polyamines participate in nearly all aspects of DNA, RNA, and protein synthesis. Polyamine accumulation is required to maintain maximum rates of cell proliferation. Blockage of polyamine accumulation by administration of DFMO and other inhibitors during accelerated cell growth results in a significant reduction of growth in a variety of cell systems. Since the only pathway to polyamine synthesis is via ornithine, synthesis depends on the activity of ODC. ODC is present in very small amounts in resting cells but can be increased many-fold within a few hours of exposure to hormones, drugs, and growth factors.

Blocking endogenous ODC has reportedly prevented transformation of rat fibroblasts by the temperature-sensitive v-src oncogene. Tumor formation in experimental animals has reportedly been prevented by inhibitors of ODC such as DFMO. DFMO has reportedly been shown to inhibit cellular replication in vitro in several malignant animal tumor cell lines, including L1210 and L5178Y leukemia, rat hepatoma, mouse mammary sarcoma (EMT6) and hamster pancreatic adenocarcinoma (H2T) (Mamont et al., 1978; Prakash et al., 1980; Marx et al., 1987).

DFMO, either alone or in combination with other agents, has proven effective in treating and/or preventing mammary carcinomas in animal models as follows. The growth of six human tumors (three mammary carcinomas, a malignant melanoma, a bladder carcinoma, and an endocervical carcinoma) was significantly decreased after DFMO treatment compared to growth in control mice. (Luk et al., 1983). In xenographs of human breast and colon carcinoma cells inoculated into nude mice, a synergistic antitumor effect was observed when DFMO was combined with mitomycin D (Takami et al., 1989).

Studies by Nishioka et al. report increases of plasma precursor amino acids of polyamines, such as arginine and ornithine, at low doses of DFMO in tissue obtained by routine cervical biopsy. DFMO was also measured as a compliance marker. Nishioka et al. proposed that polyamines and their precursor amino acids would be effective markers in analyzing the effects of DFMO, functioning as pharmacodynamic parameters, as well as biomarkers for transformation in the cervix.

Chemoprevention trials of cervical lesions using topical retinoic compounds and micronutrient have been reported; most of them being considered as negative trials. A trial by Meyskens reports histological regression of CIN II cases, but not CIN III, using topical trans-retinoic acid. The rate of regression in the treated CIN II group was reported to be 43 %, compared to 27% in the placebo group.

Determining the optimal dose of DFMO could be based on several parameters, including toxicity, modulation of polyamine synthesis markers, and/or response. In the Phase I study of Love, a dose of 0.5 g/m$^2$/day was used, being based on toxicity (Love, 1993). Studies employing modulation of polyamine synthesis markers to determine optional dose of DFMO, specifically urine polyamine markers putrescine and spermidine at a DFMO dose level of 0.2 g/m$^2$/day, have been reported in Meyskens, 1994 and Hixson, 1993. Employing polyamine synthesis markers, Meyskens, (1994) reports modulation of tissue spermidine/ spermine ratio at a dose of 0.1 g/m$^2$/day. A need continues to exist in the medical arts for methods of detecting, inhibiting and reducing the risk of developing pre-malignant tissues linked to cervical malignancies.

SUMMARY OF THE INVENTION

The present invention provides methods particularly useful in the treatment of patients with malignant cervical cancer or patients at risk of developing malignant cervical cancer. In particular applications, these methods may be employed to inhibit the progression of CIN I, II or III to cervical cancer in a patient identified as having evidence of CIN I, II or III.

In some embodiments, the method for treating, reducing the risk, and/or inhibiting malignant cervical cancer growth and/or progression of pre-malignant tissues to a malignancy, such as a patient having evidence of cervical intraepithelial neoplasia, particularly CIN III, comprises administering to a patient in need thereof a pharmaceutically acceptable preparation comprising a pharmacologically active amount of DFMO, or pharmaceutically acceptable salts thereof, in a pharmaceutically acceptable carrier.

It is contemplated and within the scope of the invention that a composition as described above will be useful for the inhibition of malignant cellular proliferation and/or of CIN I, II or III progression to cervical cancer.

Factors associated with the development or higher risk of cervical cancer include smoking, HPV patient infection, and multifocal intraepithelial neoplasia. Hence, it is contemplated that the present methods employing DFMO can be a treatment of particular application in women who smoke, have HPV infection, or have multifocal intraepithelial neoplasia of the cervix, vagina, or vulva. Another group for which chemoprevention with DFMO can be a choice is in women who are immunosuppressed due to HIV infection, rheumatologic disease, renal failure, or who use immunosuppressive medications, as well as in patients in whom surgical procedures are poorly tolerated.

Another aspect of the present invention provides a method of preventing cervical cancer and/or pre-malignant tissue development in a patient comprising administering to a patient a pharmaceutically acceptable preparation comprising a pharmacologically active amount of DFMO, or pharmaceutically acceptable salts thereof, in a pharmaceutically acceptable carrier.

It is contemplated that DFMO treatment of a patient having CIN III will inhibit cellular transformation against field cancerization and also remove cancerous cells, already transformed, through apoptosis. Thus, another aspect of the present invention provides a method of preventing and reducing the risk of cervical cancer in a patient comprising administering to a patient a pharmaceutical preparation comprising a pharmacologically active amount of DFMO or pharmaceutically acceptable salts thereof in a pharmaceutically acceptable carrier; and controlling the growth of cervical intraepithelial neoplasia cells.

The present methods in some applications may be employed as part of an overall cancer treatment regimen for the patient that include a combination therapy with DFMO together with standard regimens. It is expected that such will further enhance the effectiveness of the method of the invention. Standard treatment regimens for patients with cervical cancer and cervical intraepithelial neoplasia are well known to those in the medical arts of oncology, and are described in *Obstet Gynechological Clin North American,* 23:347–410, 1996. This reference, in so far as it provides general guidance of such routine techniques, are incorporated herein by reference for this purpose.

As used herein, a pharmacologically active amount of DFMO in the pharmaceutical preparation is defined as an amount of DFMO between about 0.01% to about 90% by weight of the preparation administered to the patient. By way of further example, a pharmacologically active amount of DFMO may be an amount that constitutes between about 30% to about 85%/wt, or even 40%, 50%, 60% or 70% to about 80%/wt of the preparation. In some embodiments, the preparation is a liquid solution taken orally by the patient.

The present invention has observed a correlation exists between the positive identification of cervical intraepithelial neoplasia (CIN) and particularly grade III (a pre-cancerous state), and the incidence of cervical cancer. The present methods therefore also advantageously employ compositions of DFMO in methods of reducing the risk of developing cervical cancer in a patient having cervical intraepithelial neoplasia comprising administering a pharmaceutical preparation comprising a pharmacologically active amount of DFMO, or pharmaceutically acceptable salts thereof.

In yet another aspect, the invention provides a method for inhibiting the growth of cervical intraepithelial neoplasia grade III in a patient. In some embodiments, the method comprises administering to a person a pharmaceutical preparation comprising a pharmacologically active amount of DFMO capable of inhibiting cervical intraepithelial neoplasia, or pharmaceutically acceptable salts of DFMO, and inhibiting intraepithelial neoplasia cell growth.

In some embodiments, the method of the present invention provides for a DFMO dose of about 0.05 gm/m$^2$/day to about 1.0 gm/m²/day, or about 0.10 gm/m²/day to about 0.95 gm/m²/day to about 0.50 gm/m²/day to about 0.95 gm/m²/day. The methods of the present invention also provide for the administration of a therapeutically effective amount of DPMO to be defined by reference to the plasma level of DFMO to be achieved in the patient being treated. Variations on these plasma DFMO levels as part of the presently described methods are included within the scope of the invention. Such variations may be indicated in the particular patient being treated, as determined by the attending physician or other health care professional.

The oral dosage forms may be tailored to achieve a plasma level of DFMO that provides therapeutic benefit to the patient with reasonable or tolerable toxicity to the patient. Oral dosage forms that have a reasonable therapeutic index may be further defined as between about 0.020 to about 10 g/m²/day, or of about 0.030 to about 5 g/m²/day, or between about 0.30 to about 1 g/m²/day, or about 0.03 g/m²/day to about 0.50 g/m²/day, or from about 0.03 g/m²/day to about 0.125 g/m²/day, or about 0.05 g/m²/day to about 1.0 g/m²/day, or about 0.06 to about 0.125 g/m²/day. Other dosage levels may be described as about 0.06 g/m²/day to about 5 g/m²/day. A dose regimen of about 10 g/m²/day is yet another treatment protocol that may be used as part of the present methods. Alternatively, the patient may be provided a DFMO treatment regimen wherein higher or lower of the dosages of DPMO noted here are used at the beginning of the treatment, with the dose being adjusted upward or downward, depending on response of the patient and/or the plasma level of DFMO observed in the patient.

An intravenous dose of DFMO, up to about 10 mg/kg (55 μmol/kg), may be employed in particular applications of the present methods. It is anticipated that the present preparations may also be administered orally, parenterally, or other route of administration or combination thereof, as part of the present methods.

As used herein, the terms "cervical intraepithelial neoplasia grade III" and "CIN III" refer to a premalignant state of disease wherein there is a spectrum of intraepithelial changes. These changes begin with a generally well-differentiated intraepithelial lesion, referred to as a low grade squamous intraepithelial lesion, and end with full thickness epithelial changes, previously referred to as carcinoma-in-situ, and currently referred to as high grade squamous intraepithelial lesion. The terms "high grade cervical intraepithelial neoplasia" and "cervical intraepithelial neoplasia grade III" and "CIN III" are used interchangeably herein.

As used herein, the term "adsorbent" is intended to mean an agent capable of holding other molecules onto its surface by physical or chemical (chemisorption) means. Such compounds include, by way of example and without limitation, powdered and activated charcoal and the like.

As used herein, the term "antioxidant" is intended to mean an agent which inhibits oxidation and thus is used to prevent the deterioration of preparations by the oxidative process. Such compounds include, by way of example and without limitation, ascorbic acid, ascorbyl palmitate, butylated hydroxyanisole, butylated hydroxytoluene, hypophophorous acid, monothioglycerol, propyl gallate, sodium ascorbate, sodium bisulfite, sodium formaldehyde sulfoxylate and sodium metabisulfite and the like.

As used herein, the term "buffering agent" is intended to mean a compound used to resist change in pH upon dilution or addition of acid or alkali. Such compounds include, by way of example and without limitation, potassium metaphosphate, potassium phosphate, monobasic sodium acetate and sodium citrate anhydrous and dihydrate and the like.

As used herein, the term "colorant" is intended to mean a compound used to impart color to liquid and solid (e.g., tablets and capsules) pharmaceutical preparations. Such compounds include, by way of example and without limitation, FD&C Red No. 3, FD&C Red No. 20, FD&C Yellow No. 6, FD&C Blue No. 2, D&C Green No. 5, D&C Orange No. 5, D&C Red No. 8, caramel, and ferric oxide, red and the like.

As used herein, the term "flavorant" is intended to mean a compound used to impart a pleasant flavor and often odor to a pharmaceutical preparation. In addition to the natural flavorants, many synthetic flavorants are also used. Such compounds include, by way of example and without limitation, anise oil, cinnamon oil, cocoa, menthol, orange oil, peppermint oil and vanillin and the like.

As used herein, the term "sweetening agent" is intended to mean a compound used to impart sweetness to a preparation. Such compounds include, by way of example and without limitation, aspartame, dextrose, glycerin, mannitol, saccharin sodium, sorbitol and sucrose and the like.

As used herein, the term "tablet antiadherents" is intended to mean agents which prevent the sticking of table formulation ingredients to punches and dies in a tableting machine during production. Such compounds include, by way of example and without limitation, magnesium stearate, talc, and the like.

As used herein, the term "tablet binders" is intended to mean substances used to cause adhesion of powder particles in table granulations. Such compounds include, by way of example and without limitation, acacia, alginic acid, carboxymethyl cellulose, sodium, compressible sugar ethylcellulose, gelatin, liquid glucose, methylcellulose, povidone and pregelatinized starch and the like.

As used herein, the term "tablet and capsule diluent" is intended to mean inert substances used as fillers to create the desired bulk, flow properties, and compression characteristics in the preparation of tablets and capsules. Such compounds include, by way of example and without limitation, dibasic calcium phosphate, kaolin, lactose, mannitol, microcrystalline cellulose, powdered cellulose, precipitated calcium carbonate, sorbitol, and starch and the like.

As used herein, the term "tablet direct compression excipient" is intended to mean a compound used in direct compression tablet formulations. Such compounds include, by way of example and without limitation, dibasic calcium phosphate (e.g., Ditab™) and the like.

As used herein, the term "tablet disintegrant" is intended to mean a compound used in solid dosage forms to promote the disruption of the solid mass into smaller particles which are more readily dispersed or dissolved. Such compounds include, by way of example and without limitation, alginic acid, carboxymethylcellulose, calcium, microcrystalline cellulose (e.g., AVICEL®), polacrilin potassium (e.g., AMBERLITE®), sodium alginate, sodium starch glycolate, and starch and the like.

As used herein, the term "tablet glidant" is intended to mean agents used in tablet and capsule formulations to reduce friction during tablet compression. Such compounds include, by way of example and without limitation, colloidal silica, cornstarch, talc, and the like.

As used herein, the term "tablet lubricant" is intended to mean substances used in tablet formulations to reduce friction during tablet compression. Such compounds include, by way of example and without limitation, calcium stearate, magnesium stearate, mineral oil, stearic acid, zinc stearate, and the like.

As used herein, the term "tablet/capsule opaquant" is intended to mean a compound used to render a capsule or a tablet coating opaque. An opaquant may be used alone or in combination with a colorant. Such compounds include, by way of example and without limitation, titanium dioxide and the like.

As used herein, the term "tablet polishing agent" is intended to mean a compound used to impart an attractive sheen to coated tablets. Such compounds include, by way of example and without limitation, carnauba wax, white wax, and the like.

It should be understood, that compounds used in the art of pharmaceutical formulation generally serve a variety of functions or purposes. Thus, if a compound named herein is mentioned only once or is used to define more than one term herein, its purpose or function should not be construed as being limited solely to that (those) named purpose(s) or function(s).

As used herein, the term DFMO is intended to mean a preparation of alpha-difluoromethylornithine in its pharmaceutically acceptable salt and/or racemic isomeric preparations of (D) and (b) DFMO. (+)-DFMO is intended to mean alpha-difluoromethylornithine having the (D)- configuration around the alpha-carbon which is the only chiral atom present in the molecule. (−)-DFMO is intended to mean alpha-difluoromethylornithine having the (L)- configuration around the alpha-carbon. (±)-DFMO is intended to mean racemic alpha-difluoromethylornithine.

Methods for the preparation of (+)-DFMO and (−)-DFMO are known. U.S. Pat. No. 4,330,559, the disclosure of which is hereby incorporated by reference in its entirety, discloses a method for the preparation of optically pure DFMO wherein racemic DFMO dihydrochloride is reacted with sodium methylate to form 3-amino-3-difluoromethyl-2-piperidone (DFMO-pip) which is subsequently crystallized in the presence of (−)-binaphthyl phosphoric acid ((−)-BNPA) to yield (−)-DFMO-pip:(−)-BNPA 1:1 addition salt crystals leaving the (+)-DFMO-pip:(−)-BNPA addition salt in solution. Following repeated recrystallization and acidification, (−)-DFMO-pip is obtained in optically pure form. The (−)-DFMO-pip is then hydrolyzed to yield (+)-DFMO. The enantiopode (+)-DFMO may be prepared according to the above procedure by employing (+)-BNPA to preferentially form the diastereomeric (+)-DFMO-pip:(+)-BNPA 1:1 addition salt crystals.

Wagner, et al. (1987), the disclosure of which is hereby incorporated by reference in its entirety, discloses a reverse phase liquid chromatographic method for the resolution of racemic DFMO to yield each enantiomer of DFMO in optically pure form.

Aldous et al. (1986) discloses a gas chromatographic analytical method for the resolution of racemic DFMO to yield each enantiomer of DFMO in optically pure form.

The compounds herein described may have asymmetric centers. All chiral, diastereomeric, and racemic forms are included in the present invention. Many geometric isomers of olefins, C=N double bonds, and the like can also be present in the compounds described herein, and all such stable isomers are contemplated in the present invention unless the specific stereochemistry or isomer form is specifically indicated. It will be appreciated that certain compounds of the present invention contain an asymmetrically substituted carbon atom, and may be isolated in optically active or racemic forms. It is well known in the art how to prepare optically active forms, such as by resolution of racemic forms or by synthesis, from optically active starting materials. Also, it is realized that cis and trans geometric isomers of the compounds of the present invention are described and may be isolated as a mixture of isomers or as separated isomeric forms.

Other features, advantages and embodiments of the invention will be apparent to those skilled in the art from the following description, accompanying data and appended claims.

Following long-standing patent law convention, the terms "a" and "an" mean "one or more" when used in this specification.

The following abbreviations are used herein and are defined as follows:

| | |
|---|---|
| DFMO | alpha-difluoromethylornithine |
| ODC | ornithine decarboxylase |
| RA | retinoic acid |
| ER | estrogen receptor |
| IGF-1 | insulin-like growth factor 1 |
| TGF-beta | transforming growth factor beta |
| MX | methotrexate |
| FU | 5-fluorouracil |
| TC | tamoxifen citrate |
| TAM | tamoxifen |
| DX | doxorubicin |
| VS | vincristine sulfate |
| MNU | 1-methyl-1-nitrosourea |
| E2 | estradiol |
| CIN III | cervical intraepithelial neoplasia grade III |
| TGI | tumor growth inhibition |
| DFMO-pip | 3-amino-3-difluoromethyl-2-pipenidone |
| BNPA | binaphthyl phosphoric acid |
| MTD | maximum tolerated dose |

BRIEF DESCRIPTION OF THE FIGURES

FIG. 3B shows proportionate change and 95% confidence intervals in arginine.

DESCRIPTION OF THE PREFERRED EMBODIMENTS

Figure 1:
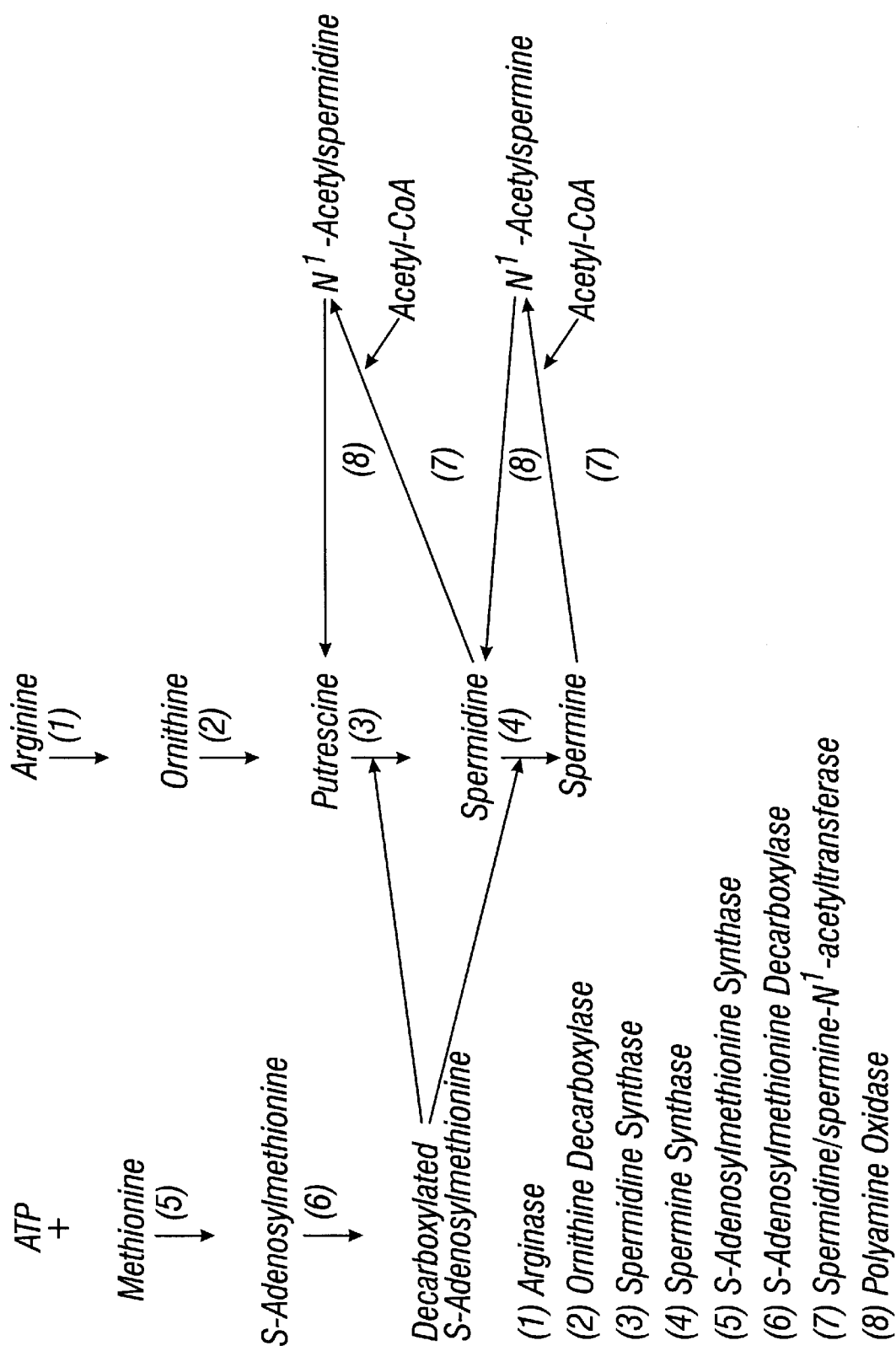
FIG. 1—Polyamine Synthesis Flow Chart.
Figure 2:
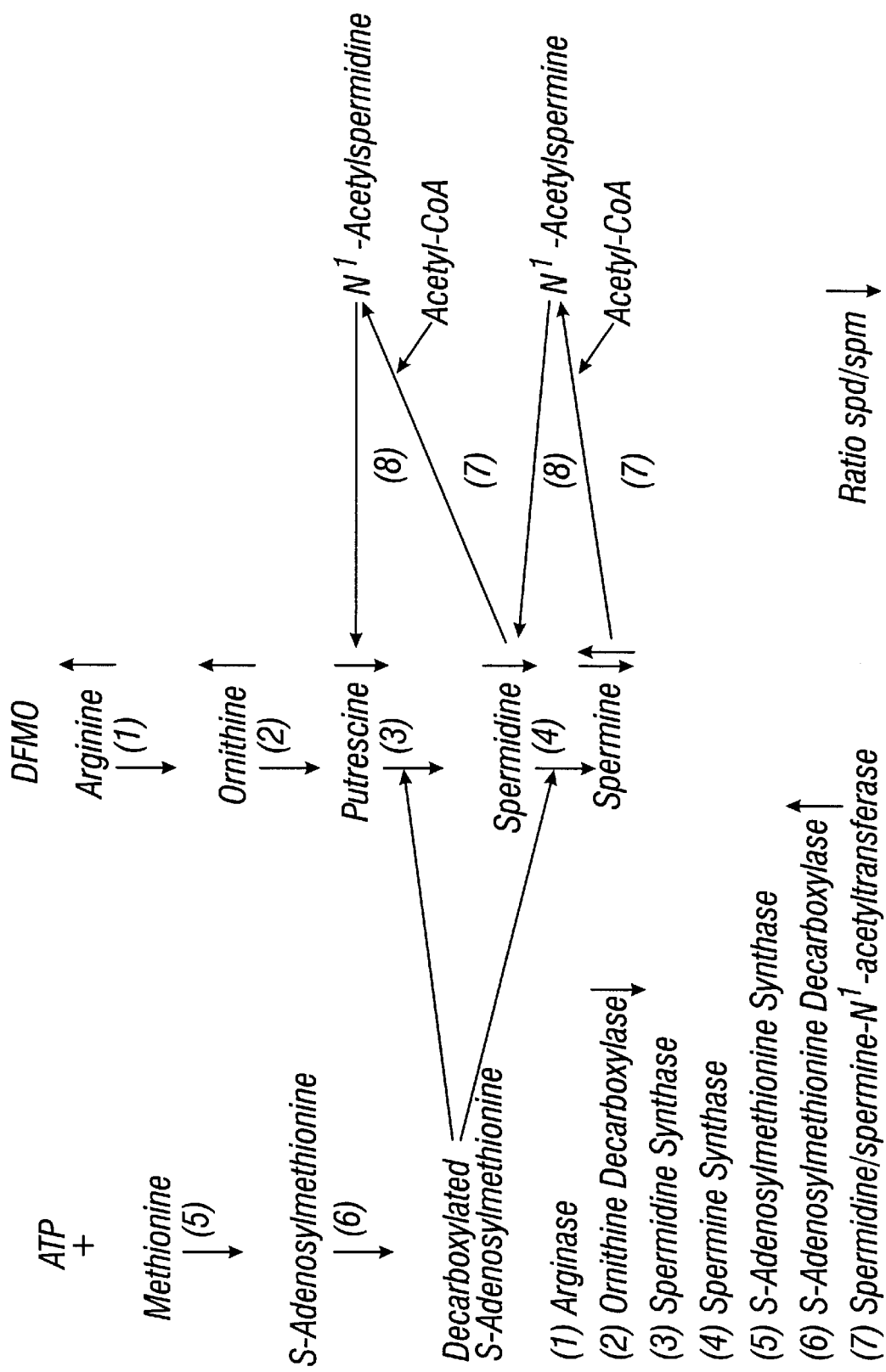
FIG. 2—Effects of DFMO on Polyamine Synthesis

In some embodiments, the present invention provides a pharmaceutical composition particularly designated for use in treating, preventing, and/or controlling the growth of and/or reducing the risk of cervical cancer and solid tumor. Particular embodiments of the method comprise administering a pharmacologically active amount of DFMO, or pharmaceutically acceptable salt thereof to a patient in need or at risk of developing cervical cancer. One factor that enhances risk of cervical cancer development is a positive identification of CIN III in a patient cervical sample. In some embodiments of the method, a pharmacologically active amount of DFMO is about 0.01% to 90% by weight of the composition or between 30% to about 85%, or about 40%, 50%, 60%, 70% or 80% by weight of the solution.

Another embodiment of the invention provides a method of treating, preventing, controlling the growth of and/or reducing the risk of developing cervical cancer and tumor in a patient comprising administering therapeutically effective amounts of a combination of a cytotoxic or cytostatic agent and DFMO, or pharmaceutically acceptable salts thereof.

In particular embodiments, the invention provides a method inhibiting cervical intraepithelial neoplasia grade III in a patient comprising administering a therapeutically effective amount of DFMO or a pharmaceutically acceptable salt thereof to the patient; and inhibiting cervical intraepithelial neoplasia cell growth.

Another embodiment of the invention provides a method of reducing the risk of developing cervical cancer in a patient having cervical intraepithelial neoplasia grade III comprising administering therapeutically effective amounts of DFMO, or pharmaceutically acceptable salts thereof to the patient.

Unless otherwise indicated, all chemicals were purchased from Aldrich Chemicals (Milwaukee, Wis.). Racemic DFMO is available from Ilex Oncology, Inc. (San Antonio, Tex.).

EXAMPLE 1

HPLC METHOD FOR POLYAMINE ANALYSIS IN TISSUE AND BLOOD

Tissues and blood samples were frozen at −70° C. until analyses were performed. Each sample was analyzed in duplicate and pre- and post-treatment samples were analyzed simultaneously. To prepare samples, a 25% tissue homogenate was prepare in ODC buffer using a Polytron homogenizer (Brinkman Instruments, Westbury, N.Y.) as described previously (15). A portion of the homogenate (20 $\mu$l) was mixed with 80 $\mu$l of 15% sulfosalicylic acid, sonicated and microcentrifuged (13,000×g) for 15 minutes at room temperature to obtain a clear supernatant for polyamine analysis. The remaining portion of the homogenate was centrifuged (700×g) for 15 minutes at 4° C. and the supernatant was analyzed for ODC activity and protein levels. Protein concentrations were determined using Bio-Rad (Richmond, Calif.) protein assay kits. A new procedure, using O-phthalaldehyde in a Dionex BioLC high-performance liquid chromatograph equipped with HPLC-CS2 column and postcolumn detection system (Dionex, Inc., Sunnyvale, Calif.) was used for determinations of arginine, ornithine, DFMO, acetylpolyamine, and free polyamine levels. Four elution buffers were prepared and filtered. Each buffer contained 1 ml phenol per liter with the following compositions: buffer A, 1 mM potassium citrate, pH 4.70, adjusted with HCl; buffer B, 0.1 M potassium citrate, pH 4.70, adjusted with HCl; buffer C, 0.2 M KCl, 10 mM KOH, 1.34 mM disodium EDTA, 11.7 mM HBP3, pH 9.20; and buffer D, 1.8 M KCl, 90 mM KOH, 12.1 mM EDTA, 0.105 M $HBO_3$, pH 9.20. The column was equilibrated with buffer A starting at 0 min, and various buffers were introduced. A sample was injected at 20 min., and recording commenced at 30 min. Samples were injected at 20 minutes and recording commenced at 30 minutes. Plasma DFMO levels are reported in pmols/ml, plasma arginine and ornithine levels in nmol/ml, tissue polyamines in nmol/1 mg soluble protein, and RBC polyamine levels in nmol/ml packed red blood cells.

EXAMPLE 2

STUDY PROTOCOL FOR EVALUATING DFMO IN TREATING CIN III

Prior to enrollment, all participants underwent a complete medical history, physical examination, pelvic examination, a Pap smear, gonorrhea and chlamydia cultures, HPV testing, colposcopic examination of the vulva, vagina and cervix, risk factors and dietary interview, and counseling regarding smoking cessation, nutrition, and sunscreen use. In addition, blood samples were collected for complete blood count; serum electrolytes, chemistry, and coagulation studies; serum levels of luteinizing hormone (LH), follicle stimulating hormone (FSH), progesterone, and estradiol; plasma levels of DFMO, ornithine, and arginine; and red blood cell (RBC) putrescine, spermidine, and spermine.

Colposcopically directed-biopsies from normal and abnormal areas were taken for permanent section and snap-frozen for studies of polyamine synthesis including ornithine decarboxylase (ODC), putrescine, spermine, and spermidine. HPV testing was performed by dot blot hybridization (VIRAPAP/VIRATYPE®, Digene Diagnostics, Washington D.C.) and negative specimens were subjected to polymerase chain reaction analysis.

Patients were identified among women attending the Colposcopy Clinic of the University of Texas M. D. Anderson Cancer Center, Department of Gynecologic Oncology. Eligible patients included the following: nonpregnant women aged 18 years and older with a biopsy-confirmed diagnosis of CIN III; a lesion involving one-third the surface area of the cervix; no history of prior malignancy; a Zubrod performance status of less than or equal to 2; and normal serum chemistries, hematologic profiles and audiometry. CIN III is a precursor of invasive cervical cancer. Women were extensively counseled about contraception and were selected based on the use of hormonal contraceptive methods, having had a bilateral tubal ligation, or being postmenopausal.

Patients were assigned to each of five decreasing doses of DFMO: 1.0, 0.5, 0.25, 0.125, and 0.06 $g/m^2$/day for 31 days. DFMO was provided by the National Cancer Institute (NCI) in elixir form in 200 mg/ml vials. Patients were provided with a 5 cc syringe to assure precise dosage.

Post-treatment evaluation included the following: colposcopically directed biopsies from normal and abnormal areas for polyamine synthesis analysis, colposcopically directed loop electrosurgical excision (LEEP) of the cervix for complete histological study and definitive treatment. Blood samples were collected for determination of post-treatment plasma levels of DFMO, ODC, putrescine, spermidine, spermine, ornithine and arginine and RBC levels of putrescine, spermidine, and spermine. All histological specimens were evaluated and responses were determined by histological regression of the lesion.

Baseline polyamine values between colposcopically normal and abnormal tissue areas were compared among all patients. Post-treatment DFMO values in plasma are compared by dose level. The effect of DFMO treatment on polyamine values was assessed by the differences between baseline and post-treatment polyamine values at each DFMO dose level in biopsy specimens from colposcopically abnormal tissue areas, in plasma, and in RBC. In addition, proportionate changes (and 95% confidence intervals) in polyamine tissue, plasma, and RBC, were estimated as the change due to DFMO treatment [(polyamine value post-DFMO—polyamine value at baseline) divided by polyamine value at baseline]. Because of the large variability in all polyamine measurements, data were analyzed by the Wilcoxon's matched-pairs signed-rank test. Statistical significance was set at an alpha of 0.05 based on two-sided test.

EXAMPLE 3

PREPARATION OF SOLUTIONS CONTAINING DFMO FOR TREATMENT OF CIN III

The present example details the DFMO preparation that was used in the study of CIN III in humans.

As will be appreciated by those of skill in the art, the preparations may be formulated according to techniques well known to those of skill in the art (Remingtons Pharmaceutical Sciences, 18 edition). A DFMO elixir (200 mg/ml) may be prepared at a concentration and provided to a patient so as to achieve a dose of between about 0.060 and about 0.125 $g/m^2$/day for a treatment period of at least 30 days. The solution was prepared by the National Cancer Institute in elixir form and shipped to MD Anderson Cancer Center for the present studies.

EXAMPLE 4

DFMO DOSE LEVELS AND CERVICAL INTRA EPITHELIAL NEOPLASIA

Women suspected of having CIN I to CIN III were biopsied colposcopically in both normal and abnormal regions of the cervix to determine the severity or extent of disease progression (See Example 2). Thirty patients with biopsy-proven CIN III underwent a Papanicolaou (PAP) smear and colposcopically directed biopsies, using 3–6% acetic acid, for histology and for polyamine synthesis biomarkers. Patients also underwent complete medical history, nutritional survey, sexual behavior interview, physical exam, colposcopy, HPV testing, blood counts, serum chemistries, audiogram; plasma DMSO, ornithine and arginine measurements, erythrocyte polyamine measurement, tissue DFMO, ODC and polyamine measurement, and smoking cessation counseling. Blood was drawn for determinations of levels of red blood cell polyamine synthesis markers and the plasma polyamine precursors ornithine and arginine levels according to the method of Example 1. Patients were assigned to one of five doses of DFMO: 1.0, 0.5, 0.25, 0.125, and 0.06 $g/m^2$/day for 31 days. Patients then underwent biopsies and repeat blood sampling for polyamine synthesis markers followed by loop electrosurgical excision of the cervix for complete histopathological study. The spermidine/spermine ratio was evaluated for tissue measurements as a way of decreasing variability and determining the pharmacological effect of DFMO.

Patients studied included two groups: women with high grade lesions and women infected with high risk oncogenic HPV types. The rationale for using patients with high grade lesions is that such lesions are more likely to progress to invasive cancer; up to 36% of (CIN) lesions progressed in a series of studies in which 353 patients were followed without treatment over periods of 3 months to 30 years. The rationale for selecting patients with oncogenic HPV lesions comes from the cross-sectional and cohort studies demonstrating greatly increased risk of CIN and of cervical cancer in women who are HPV-positive compared with those who are HPV-negative.

The demographic characteristics of the study population were as follows. The median age of the study group was 27 years (range 20 to 41 years) and 70% were non-Hispanic whites, 23% Hispanics, and 7% African-Americans. No differences in age or racial/ethnic distribution were observed between DFMO dose levels. Eighty-three percent of the women were positive for HPV by dot blot hybridization and polymerase chain reaction. All patients were negative for Neisseria Gonorrhea.

To determine whether polyamine levels differ between normal and abnormal tissues, baseline differences in tissue polyamines between colposcopically normal and abnormal tissue areas were measured separately and are shown in Table 1. Higher ODC, putrescine, spermidine and spermine values were observed in abnormal tissue areas compared to normal tissue areas; whereas a slightly lower spermidine:spermine (SPD:SPM) ratio was observed in abnormal tissue areas. The differences in ODC and SPD:SPM ratio between baseline normal and abnormal tissue areas were statistically significant ($p<0.05$).

TABLE 1

Baseline differences in polyamine values between colposcopically normal and abnormal tissue

| Polyamine | Normal Tissue | Abnormal Tissue | Difference | p* |
|---|---|---|---|---|
| ODC (nmol/ml) | | | | |
| - mean | 282.6 | 338.3 | 55.7 | 0.03 |
| - std. error | 48.4 | 64.4 | | |
| - median | 188.6 | 214.8 | | |
| - minimum | 26.8 | 65.6 | | |
| -maximum | 1151.3 | 1811.7 | | |
| Putrescine (nmol/1 mg soluable protein) | | | | |
| - mean | 1505.0 | 1664.2 | 184.2 | 0.97 |
| - std error | 245.4 | 328.4 | | |
| - median | 948.5 | 1462.0 | | |
| - minimum | 364.0 | 68.0 | | |
| - maximum | 5265.0 | 9144.0 | | |
| Spermidine (nmol/1 mg soluable protein) | | | | |
| - mean | 5105.0 | 5220.4 | 114.9 | 0.99 |
| - std error | 735.9 | 657.1 | | |
| - median | 3562.0 | 3802.0 | | |
| - minimum | 1737.0 | 812.0 | | |
| - maximum | 19108.0 | 15400.0 | | |
| Spermine (nmol/1 mg soluable protein) | | | | |
| - mean | 4299.7 | 5426.4 | 1126.7 | 0.13 |
| - std error | 646.8 | 765.4 | | |
| - median | 3342.0 | 3969.0 | | |
| - minimum | 957.0 | 846.0 | | |
| -maximum | 18197.0 | 16831.0 | | |
| SPD:SPM Ratio (nmol/1 mg soluable protein) | | | | |
| - mean | 1.26 | 1.19 | −0.065 | −0.0012 |
| - std error | 0.07 | 0.23 | | |

TABLE 1-continued

Baseline differences in polyamine values between colposcopically normal and abnormal tissue

| Polyamine | Normal Tissue | Abnormal Tissue | Difference | p* |
|---|---|---|---|---|
| - median | 1.23 | 0.97 | | |
| - minimum | 0.70 | 0.55 | | |
| - maximum | 2.15 | 7.46 | | |

*Wilcoxon's signed-rank test

The mean number of treatment days was 30 days (median 31 days, range 22 to 33 days). Patients missed an average of 3.6 days of DFMO (range 1 to 8 days). Post-treatment DFMO plasma levels are shown in Table 2. A large, but not statistically significant, difference in mean DFMO plasma levels between patients in the highest and lowest DFMO dose levels was detected. Although women in the highest DFMO dose level had higher DFMO plasma values and women in the lowest DFMO dose level had lower DFMO plasma levels, a large variability and overlap in DFMO plasma values was observed across dose levels. Furthermore, women in the intermediate dose groups showed little variation in DFMO plasma values. Plasma DFMO values ranged from 0 pmol/ml (below detectable values) in the dose group 0.125 g/m²/day to 621.9 pmol/ml in the dose group 1.0 g/m²/day.

TABLE 2

Post-treatment plasma DFMO levels (pmol/ml)

| DFMO Dose* | n | Mean(se)† | Median | Minimum | Maximum |
|---|---|---|---|---|---|
| 1.000 | 6 | 146.3 | (96.4) | 73.9 | 1.86219 |
| 0.500&  | 5 | 23.0 | (8.2) | 24.7 | 0.642.1 |
| 0.250 | 6 | 23.9 | (4.6) | 28.9 | 2.831.4 |
| 0.125 | 6 | 16.5 | (5.3) | 24.5 | **33.2 |
| 0.060 | 6 | 5.9 | (0.7) | 5.4 | 4.38.8 |

*g/m²/day
†standard error
& One patient excluded from analysis for protocol violation
** Less than minimum value detected The median elapsed time between the final DFMO dose and the collection of post-treatment biological specimens was 3.5 hours (range 1 to 195.5 hours). In six patients the elapsed time between the final dose and specimen collection was>5 hours (14 hours n=1, 15 hours n=2, 16 hours n=2, 196 hours n=1). The elapsed time between final dose and post-treatment collection of biological specimen appears to have an effect on the measured DFMO plasma levels but not on polyamine markers in tissue, plasma, or RBC. Lower DFMO plasma levels were observed among 5 of 6 women with elapsed time>5 hours, ranging from 0 pmol/ml (below detectable values) in the patient with the largest elapsed time (196 hours) to 8.4 pmol/ml in a patient with an elapsed time of 15 hours.

Figure 3A:
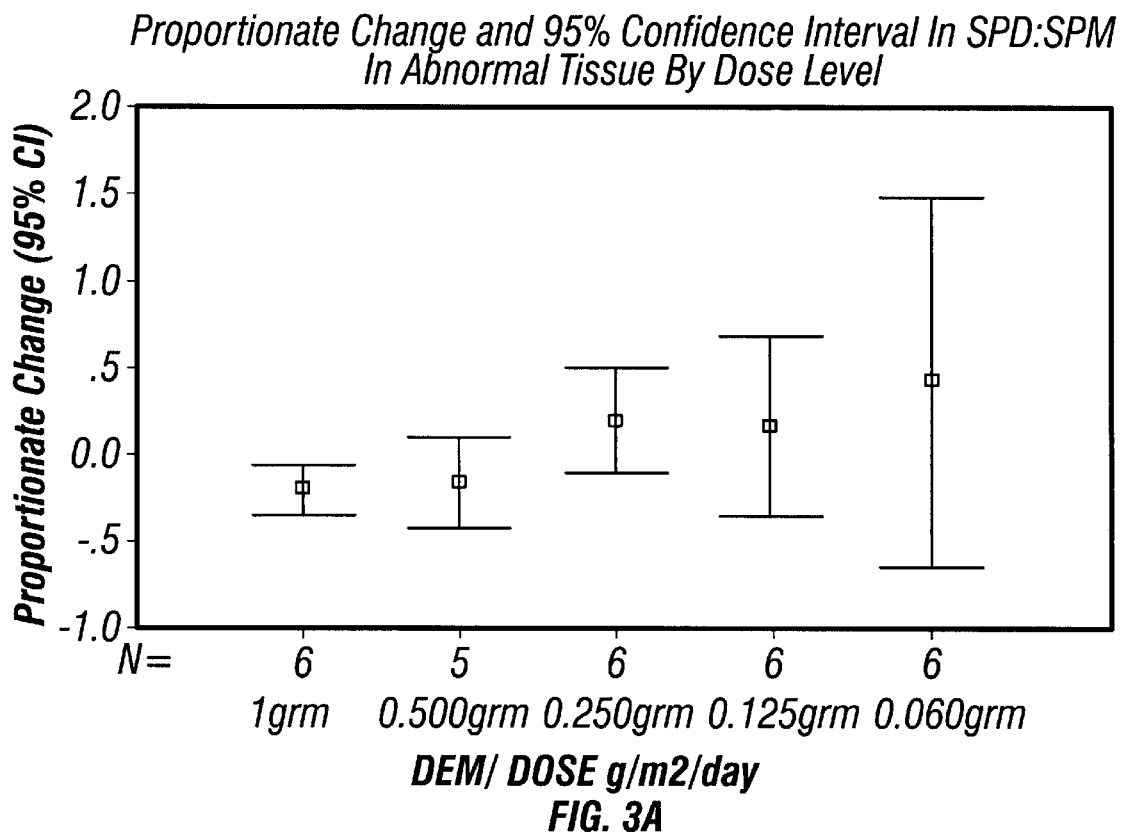
FIG. 3A–FIG 3B—FIG. 3A shows proportionate change and 95% confidence intervals in SPD:SPM in abnormal tissue by dose level.
Figure 3B:
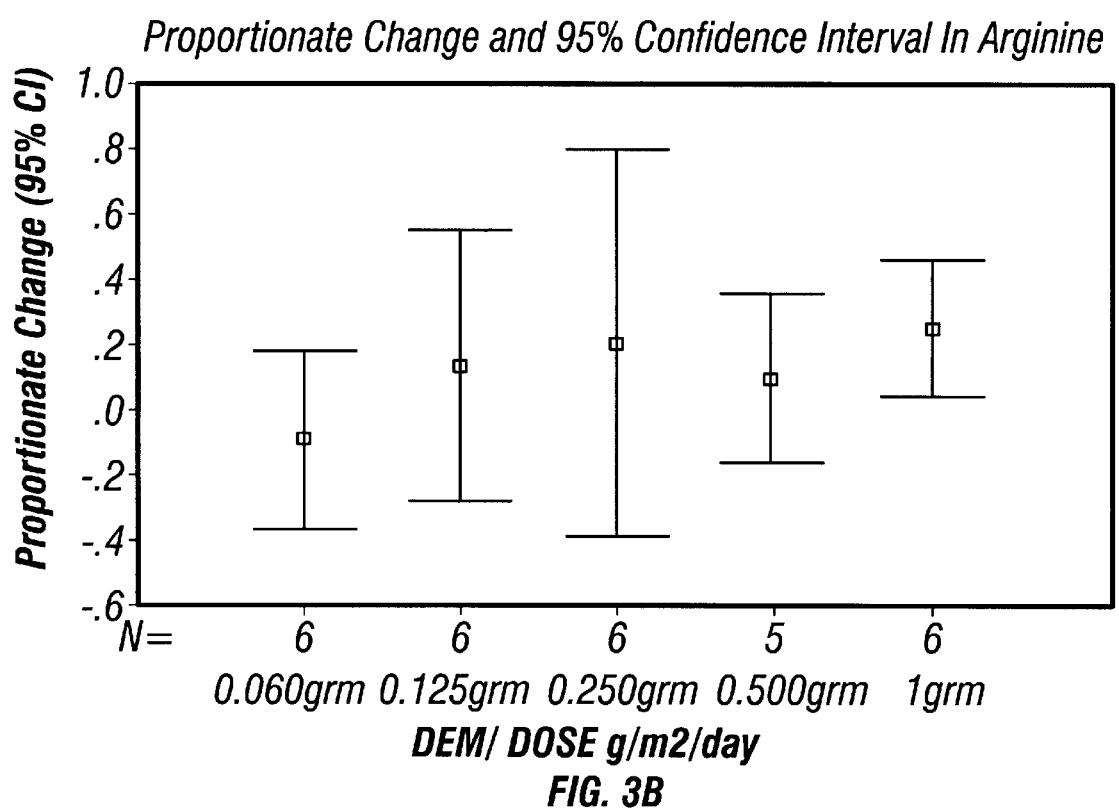

It has now been discovered that DFMO provides a therapeutic alternative in treating CIN III. The effect of DFMO on tissue and plasma polyamine values was determined and the median values at baseline and post-treatment are presented in Table 3. Statistically significant modulation (P<0.05) of tissue SPD:SPM ratios and plasma arginine was observed among patients in the highest DFMO dose level (1.0 g/m²/day). A modulation effect on tissue SPD:SPM ratio was detected among women receiving 0.500 g/m²/day of DFMO and on plasma arginine of women receiving 0.500 and 0.125 g/m²/day of DFMO (FIG. 3). No modulation on any polyamine marker was observed among patients in the lowest DFMO dose group (0.06 g/m²/day).

TABLE 3

Comparison between baseline and post-treatment polyamine median values in: abnormal tissue, plasma, and RBC by dose level (n = 29)

| Dose Level g/m2/day | ODC median (range) | Putrescine median (range) | Spermidine median (range) | Spermine median (range) | SPD:SPM Ratio* median (range) |
|---|---|---|---|---|---|
| 1,000 | | | | | |
| Baseline | 168 (66–675) | 640 (496–1586) | 3993 (1270–15400) | 3951 (1194–16831) | 1.06 (0.91–1.21)** |
| Post-treatment | 190 (75–627) | 885 (255–4943) | 6562 (1628–14655) | 6839 (1924–21832) | 0.90 (0.53–0.97) |
| 0.500 | | | | | |
| Baseline | 182 (103–294) | 490 (68–1925) | 2046 (812–11023) | 2199 (846–9229)* | 1.00 (0.93–1.19) |
| Post-treatment | 63 (23–395) | 243 (154–1532) | 3267 (1601–12564) | 3763 (1663–16050) | 0.87 (0.61–0.97) |
| 0.250 | | | | | |
| Baseline | 155 (81–1,812) | 1161 (464–2019) | 4115 (2166–5873) | 4226 (2542–7997) | 0.88 (0.64–1.19) |
| Post-treatment | 204 (98–327) | 822 (599–2458) | 3832 (1972–20537) | 3986 (1847–13070) | 1.07 (0.72–1.57) |
| 0.125 | | | | | |
| Baseline | 327 (106–660) | 1580 (590–1867) | 3728 (1932–7483) | 3777 (2139–11754) | 0.87 (0.64–1.46) |
| Post-treatment | 236 (40–1534) | 724 (113–1119) | 2854 (2120–9895) | 3019 (1477–9498) | 0.99 (0.83–1.44) |
| 0.60 | | | | | |
| Baseline | 331 (134–598) | 1465 (1056–1924) | 7044 (2895–10513) | 6284 (1410–14809) | 0.83 (0.55–7.46) |
| Post-treatment | 659 (634–1054) | 579 (130–2276) | 6413 (3232–11219) | 55718 (2273–15992) | 1.14 (0.50–1.49) |

| Dose Level (g/m2/day) | Plasma Ornithine median (range) | Plasma Arginine median (range) | RBC Putrescine median (range) | RBC Spermidine median (range) | RBC Spermine median (range) |
|---|---|---|---|---|---|
| 1,000 | | | | | |
| Baseline | 56 (29–73) | 78 (47–115)*** | 40 (26–90) | 15660 (10877–19313) | 11332 (9750–36194) |
| Post-treatment | 64 (30–110) | 106 (5–144) | 48 (0–91) | 17084 (14489–21468) | 12825 (8993 - 25928) |
| 0.500 | | | | | |
| Baseline | 45 (35–61) | 62 (51–87) | 99** (34–181) | 17811 (12481–24924) | 9773 (6377–24514) |
| Post-treatment | 47 (43–50) | 76 (42–95) | 75 (0–88) | 15980 (14022–25436) | 8648 (3669–17428) |
| 0.250 | | | | | |
| Baseline | 52 (35– | 80 (47– | 91 (63– | 16229 (11076– | 16115 (6581– |

TABLE 3-continued

Comparison between baseline and post-treatment polyamine median values in: abnormal tissue, plasma, and RBC by dose level (n = 29)

|  |  |  |  |  |  |
|---|---|---|---|---|---|
|  | 76) | 113) | 205) | 25575) | 32611) |
| Post-treatment | 57 | 92 | 88 | 12383 | 12608 |
|  | (39– | (47– | (0– | (7629– | (5274– |
|  | 71) | 126) | 196) | 19926) | 18800) |
| 0.125 |  |  |  |  |  |
| Baseline | 51 | 73 | 73 | 12132 | 25491 |
|  | (27– | (55– | (29– | (6931– | (10340– |
|  | 63) | 113) | 135) | 15003) | 32780) |
| Post-treatment | 65 | 81 | 89 | 16271 | 21391 |
|  | (31– | (40– | (0– | (2637– | (12358– |
|  | 85) | 141) | 369) | 22179) | 40780) |
| 0.060 |  |  |  |  |  |
| Baseline | 40 | 83 | 126 | 14311 | 10612 |
|  | (20– | (73– | (109– | (7399– | (4739– |
|  | 67) | 100) | 232) | 27724) | 17583) |
| Post-treatment | 40 | 67 | 108 | 15823 | 9331 |
|  | (25– | (55– | (74– | (10601– | (6392– |
|  | 58) | 128) | 305) | 20645) | 23380) |

*Spermidine: Spermine ratio
**Wilcoxon Matched - Pairs Signed-Ranks Test p<.05

EXAMPLE 5

DETERMINATION OF (+)- AND (–)-DFMO IN BODY FLUIDS

A partial or complete histological response was detected in 50% of the participants.

Complete responses (negative histology) were detected in 5 patients and partial responses (histological regression to CIN I or II) were detected in 10 patients (Table 4). These observations were confirmed with computer-assisted quantitative histopathological analysis of feulgen stained slides. When polyamine markers were studied looking at differences between responders and non-responders, only tissue spermidine was significantly different. Observable therapeutic responses occurred at all dose levels. Thus, the present data demonstrates the utility of DFMO in preventing and reducing the risk of cervical cancer by treating and controlling the growth of CIN III cells.

TABLE 4

Number of histological responses by DFMO dose level

| Dose | Response | | | |
|---|---|---|---|---|
| (g/m2/day) | Complete | Partial | No Response | Total |
| 1.00 | 0 | 3 | 3 | 6 |
| 0.500 | 0 | 2 | 3 | 5 |
| 0.250 | 1 | 3 | 2 | 6 |
| 0.125 | 2 | 2 | 2 | 6 |
| 0.060 | 2 | 0 | 4 | 6 |
| Total | 5 | 10 | 14 | 29 |

EXAMPLE 6

DOSAGE FORMS OF DFMO IN THE TREATMENT OF CIN AND PREVENTION/TREATMENT OF CERVICAL CANCER

The pharmaceutical composition that may be used in the methods of the present invention can be administered by a variety of routes such as, by way of example and without limitation: intraperitoneal, intra-articular, intra-arterial, intracardiac, intracavity, intradermal, intrathecal, intrathoracic, percutaneous, intravascular, intravenous, intracoronary, intramuscular or subcutaneous injection; or oral, buccal, rectal or sublingual administration. Such methods of administration and others contemplated within the scope of the present invention may be formulated according to techniques known to the skilled artisan. When used to prevent or reduce the risk of cervical cancer, DFMO will generally be administered chronically and at lower doses than those used for treating or controlling the growth of the cancer.

The present pharmaceutical composition can be provided in a variety of dosage forms such as, by way of example and without limitation, solution, suspension, cream, ointment, lotion, capsule, tablet, caplet, gelcap, suppository, enema, transdermal patch, implant, gel, injectable, i.v. infusion bag or bottle, concentrate, dressing, elixir, syrup, emulsion, film, granule, gum, insert, jelly, foam, paste, pastille, pellet, spray, swab, tape, troche, lozenge, disk, magma, poultice, or wafer.

Methods for the preparation of the dosage forms contemplated herein are described in the included examples or in the references cited, the disclosures of which are hereby incorporated herein in their entirety. Any ingredients used in the present formulation should not degrade or decompose a significant portion of the DFMO or other therapeutic compound(s) used prior to administration.

The term "unit dosage form" is used herein to mean a single or multiple dose form containing a quantity of the formulation, said quantity being such that one or more predetermined units are normally required for a single therapeutic administration. In the case of multiple dose forms, such as scored tablets, said predetermined unit will be one fraction, such as a half or quarter of a scored tablet, of the multiple dose form.

It is contemplated that a combination of rapid-acting, short-acting, fast-releasing, long-acting, colorectal release, sustained release, controlled release, pulsatile release, gastric release, enteric release, extended release, timed release or slow release dosage forms may be used in the present invention.

Pharmaceutical Formulation and Administration

For injection, the pharmaceutical composition can be formulated, for reconstitution with an appropriate solution, as, for example and without limitation: freeze dried, rotary dried or spray dried powders; amorphous powders; or granules, precipitates or particulates. For injection, the composition may also be formulated as suspensions or liquids in the appropriate solutions, such as, by way of example and without limitation, water, aqueous solvents, nonprotic solvents, protic solvents, hydrophilic solvents, hydrophobic solvents, polar solvents, nonpolar solvent and/or combinations thereof, optionally containing stabilizers, pH modifiers, surfactants, bioavailability modifiers and/or combinations thereof. The pharmaceutical composition can be administered in the form of a depot injection or implant preparation which may be formulated in such a manner as to permit a sustained release of the active ingredient. The composition can be compressed into pellets or small cylinders and implanted subcutaneously or intramuscularly as depot injections or implants. Implants can employ inert materials such as biodegradable polymers or synthetic silicones, for example, SILASTIC™, silicone rubber-manufactured by the Dow-Corning Corporation.

For oral, buccal, and sublingual administration, the pharmaceutical composition of the invention may be administered as either solutions or suspensions in the form of gelcaps, caplets, tablets, capsules or powders. For rectal administration, the compounds of the invention may be administered in the form of suppositories, ointments, enemas, tablets and creams for release of compound in the intestines, sigmoid flexure and/or rectum. It is contemplated that the pharmaceutical formulation can be formulated as, for example and without limitation, freeze dried, rotary dried or spray dried powders; amorphous or crystalline powders; or granules, precipitates or particulates. The solids used can be either free-flowing or compressed. The pharmaceutical formulation can comprise by way of example and without limitation, water, aqueous solvents, nonprotic solvents, protic solvents, hydrophilic solvents, hydrophobic solvents, polar solvents, nonpolar solvent, emollients and/or combinations thereof, optionally containing stabilizers, pH modifiers, surfactants, perfumes, astringents, cosmetic foundations, pigments, dyes, bioavailability modifiers and/or combinations thereof.

The pharmaceutical composition can also be administered as liquid suspensions or solutions using a sterile liquid, such as an oil, water, an alcohol, or mixtures thereof, with or without the addition of a pharmaceutically suitable surfactants, suspending agent, or emulsifying agent for oral or parenteral administration.

For liquid preparations, the pharmaceutical composition can be formulated suitably with oils, for example, fixed oils, such as peanut oil, sesame oil, cottonseed oil, corn oil and olive oil; fatty acids, such as oleic acid, stearic acid and isotearic acid; and fatty acid esters, such as ethyl oleate, isopropyl myristate, fatty acid glycerides and acetylated fatty acid glycerides; with alcohols, such as ethanol, isopropanol, hexadecyl alcohol, glycerol and propylene glycol; with glycerol ketals, such as 2,2-dimethyl-1,3-dioxolane-4-methanol; with ethers, such as poly(ethyleneglycol) 450, with petroleum hydrocarbons, such as mineral oil and petrolatum; with water, or with mixtures thereof; with or without the addition of a pharmaceutically suitable surfactant, suspending agent or emulsifying agent.

The solid unit dosage form of the invention will comprise DFMO and can be combined with conventional carriers, for example, binders, such as acacia, corn starch or gelatin; disintegrating agents, such as, corn starch, guar gum, potato starch or alginic acid; lubricants, such as, stearic acid or magnesium stearate; and inert fillers, such as lactose, sucrose or corn starch. The solid dosage form may comprise granules. As used herein, the term "granule" is taken to mean particle, crystal, powder, particulate, minitablet, compact or other similar solid forms. The granules used in the invention may display diffusion and/or dissolution controlled release rate profiles according to the components from and processes by which they are made.

For gelcap preparations, the pharmaceutical formulation may include oils, for example, fixed oils, such as peanut oil, sesame oil, cottonseed oil, corn oil and olive oil; fatty acids, such as oleic acid, stearic acid and isostearic acid; and fatty acid esters, such as ethyl oleate, isopropyl myristate, fatty acid glycerides and acetylated fatty acid glycerides; with alcohols, such as ethanol, isopropanol, hexadecyl alcohol, glycerol and propylene glycol; with glycerol ketals, such as 2,2-dimethyl-1,3-dioxolane-4-methanol; with ethers, such as poly(ethylene glycol) 450, with petroleum hydrocarbons, such as mineral oil and petrolatum; with water, or with mixtures thereof; with or without the addition of a pharmaceutically suitable surfactant, suspending agent or emulsifying agent.

Oils can also be employed in the preparation of formulations of the soft gelatin type. Water, saline, aqueous dextrose and related sugar solutions, and glycerols may be employed in the preparation of suspension formulations which may suitably contain suspending agents, such as pectin, carbomers, methyl cellulose, hydroxypropyl cellulose or carboxymethyl cellulose, as well as buffers and preservatives. Soaps and synthetic detergents may be employed as surfactants and as vehicles for detergent compositions. Suitable soaps include fatty acid alkali metal, ammonium, and triethanolamine salts. Suitable detergents include cationic detergents, for example, dimethyl dialkyl ammonium halides, alkyl pyridinium halides, and alkylamine acetates; anionic detergents, for example, alkyl, aryl and olefin sulfonates, alkyl, olefin, ether and monoglyceride sulfates, and sulfosuccinates; nonionic detergents, for example, fatty amine oxides, fatty acid alkanolamides, and poly(oxyethylene)-block-poly(oxypropylene) copolymers; and amphoteric detergents, for example, alkyl β-aminopropionates and 2-alkylimidazoline quaternary ammonium salts; and mixtures thereof.

The formulation may also comprise adsorbents, antioxidants, buffering agents, colorants, flavorants, sweetening agents, tablet antiadherents, tablet binders, tablet and capsule diluents, tablet direct compression excipients, tablet disintegrants, tablet glidants, tablet lubricants, tablet or capsule opaquants and/or tablet polishing agents.

As used herein, the term "adsorbent" is intended to mean an agent capable of holding other molecules onto its surface by physical or chemical (chemisorption) means. Such compounds include, by way of example and without limitation, powdered and activated charcoal and the like.

As used herein, the term "antioxidant" is intended to mean an agent which inhibits oxidation and thus is used to prevent the deterioration of preparations by the oxidative process. Such compounds include, by way of example and without limitation, ascorbic acid, ascorbyl palmitate, butylated hydroxyanisole, butylated hydroxytoluene, hypophophorous acid, monothioglycerol, propyl gallate, sodium ascorbate, sodium bisulfite, sodium formaldehyde sulfoxylate and sodium metabisulfite and the like.

As used herein, the term "buffering agent" is intended to mean a compound used to resist change in pH upon dilution or addition of acid or alkali. Such compounds include, by way of example and without limitation, potassium metaphosphate, potassium phosphate, monobasic sodium acetate and sodium citrate anhydrous and dihydrate and the like.

As used herein, the term "colorant" is intended to mean a compound used to impart color to liquid and solid (e.g., tablets and capsules) pharmaceutical preparations. Such compounds include, by way of example and without limitation, FD&C Red No. 3, FD&C Red No. 20, FD&C Yellow No. 6, FD&C Blue No. 2, D&C Green No. 5, D&C Orange No. 5, D&C Red No. 8, caramel, and ferric oxide, red and the like.

As used herein, the term "flavorant" is intended to mean a compound used to impart a pleasant flavor and often odor to a pharmaceutical preparation. In addition to the natural flavorants, many synthetic flavorants may also be used. Such compounds include, by way of example and without limitation, anise oil, cinnamon oil, cocoa, menthol, orange oil, peppermint oil and vanillin and the like.

EXAMPLE 7

METHOD OF TREATMENT OF CERVICAL INTRAEPITHELIAL NEOPLASIA CANCER WITH DFMO

The course and duration of administration of and the dosage requirements for the formulation of the present invention will vary according to the subject being treated, the formulation used, the method of administration used, the severity and type of cervical cancer or tumor being treated, the coadministration of other drugs and other factors.

Although each unit dosage form contains therapeutically effective amounts of DFMO, it may be necessary to administer more than one such unit dosage form in order to obtain the full therapeutic benefit of the DFMO. More particularly, since DFMO may require moderately high doses, vide supra, it is very likely that more than one unit dosage from will need to be administered to a patient in order to obtain the full therapeutic benefit of DFMO.

For example, consider that the average 65–70 Kg human has a body surface area of about 1.65 $m^2$ to about 1.8 $m^2$, or about 1.73 $m^2$. If DFMO is administered at a dosage of up to about 1 $g/m^2$/day, then a patient would have to receive about 1.7 g of DFMO/day, about 3½ tablets containing about 0.5 g of DFMO. Correspondingly, if the dosage administered is about 0.25 $g/m^2$/day then a patient would have to receive about 0.4 g/day, about 1 tablet containing 0.5 g of DFMO.

A study of DFMO on women with CIN III has been completed. In this study, 30 patients with biopsy-proven CIN III were assigned to receive one of 5 doses of DFMO (1.0, 0.5, 0.25, 0.125, or 0.06 $g/m^2$/day) orally for 31 days. A significant percentage (17%) of the patients expressed a complete histological response and 33% had histological regression to CIN I or II, although responses were not dose-related.

These results demonstrate the utility of the present invention as a therapy for the treatment of CIN I, II or III in HIV-infected patients, as well as patients with CIN I, II or III without HIV infection.

EXAMPLE 8

GROWTH INHIBITORY EFFECTS OF α-DIFLUOROMETHYLORNITHINE (DFMO) ON HUMAN CERVICAL CARCINOMA (HCC) CELL LINES IN VITRO

In this example the effects of DFMO on the growth of 9 HCC cell lines is demonstrated. This example demonstrates the utility of the present invention for treating and inhibiting cervical cancer and progression of CIN-characterized tissue to cervical cancer.

DFMO was found to inhibit the growth of all cell lines examined irrespective of their human papillomavirus and p53 status. The DFMO concentrations required for 50% growth inhibition on day 5 ranged from 15 $\mu$M to >5 mM. These concentrations are relevant because Phase I studies of single dose pharmacokinetics reported plasma levels ranging from 14 to 50 $\mu$M. The effects were time dependent with inhibition detectable first after 2 days of treatment. These findings suggest that cervical malignancies and presumably also CIN lesions may respond to DFMO in vivo.

Chemicals

2-Difluoromethyl-ornithine (DFMO) was dissolved in distilled water at a concentration of 1 M and sterilized by filtration through a 0.22-um-pore membrane. Aliquots were stored at −80° C. and used only once after thawing.

4-HPR was obtained from McNeil Pharmaceutical Research. It was dissolved in dimethylsulfoxide (DMSO) at a concentration of 10 mM, and stored in the dark at −20° C. Stock solutions were diluted to the appropriate concentrations with growth medium just prior to use.

Growth Inhibition Assays

The human cervical carcinoma cell lines C-33A, C-4I, C-4II, Caski, HeLa, HT-3, MS751, and SiHa were purchased from the American Type Culture Collection (ATCC, Rockville, Md.). The ME 180 cells were obtained from Dr. Nicholas Donato (M.D. Anderson Cancer Center, Houston, Tex.). The details on the isolation of these cell lines and some of their properties are outlined in the ATCC catalog. All cells were grown as monolayers in a 1:1 mixture of Dulbecco's modified Eagle's medium: Ham's F12 medium (DMEM/F12) supplemented with 10% fetal bovine serum (FBS) and antibiotics (100 u/ml penicillin and 100 ug/ml streptomycin) in a humidified incubator at 37° C. in an atmosphere of 5% CO2.

Exponentially growing cells were seeded at densities ranging from 1000 to 3000 cells per well in 96-well cluster tissue culture plates and treated the next day with increasing concentrations of DFMO or 4-HPR for 5–7 days. Cell cultures grown in medium alone served as controls. Control cultures received the same amount of DMSO in 4-HPR treated cultures. Half of the growth medium with or without the supplementation of drugs was changed after 3 days of treatment. Cell numbers were estimated everyday by using the sulforhodamine B (SRB) assay with a slight modification. The medium was discarded and the adherent cells were fixed in situ by adding to each well 100 ul of cold tichloroacetic acid (TCA), 10% (w/v) and incubating for 60 minutes at 4° C. The wells were then rinsed five times with deionized water and air dried. Each well then received 50 ul of SRB (Sigma Chemical Co., St. Louis, Mo.) solution (0.4% w/v in 1% acetic acid) and the plates were incubated for 10 min at room temperature. Unbound SRB was removed by rinsing five times with 1% acetic acid. After the plates were dried, the densities were read using a microtiter plate reader at 492 nm. 8 replicate wells were used for each analysis. The percentage of growth inhibition (GI) was calculated by using the equation: %GI=(1−Nt/Nc)*100 where Nt and Nc represent the optical density in treated and control cultures respectively. ID50 which is the drug concentration causing cell growth inhibition by 50% was determined by interpolation from dose response curves.

(3H)Thymidine uptake and incorporation into DNA

Exponentially growing cells (3000 cells/well, 96-well plate) were incubated in the absence or presence of increasing concentration of DFMO or 4-HPR. (3H)Thymidine was added to cell cultures for the final 6 hours of incubation. The plates were frozen in −20° C. and thereafter thawed and harvested by cell harvester (Cambridge Technology, Inc.). Filters were washed three times with 5% trichloroacetic acid and twice with 90% ethanol, air-dried and assayed for (3H)thymidine by liquid scintillation counting.

C33A cells were plated on 10 cm diameter dishes one day before DFMO treatment. At pre-established time of treatment with 500 uM DFMO, cells were harvested by tripsinization and centrifuged at 300×g for 5 minutes, washed, and processed as below.

Two different methods will be evaluated for DNA labeling:

(1) The 300×g centrifuged cell pellet was fixed in cold 70% ethanol at 4° C. for 60 minutes. The cells were then centrifuged, washed in PBS and resuspended in )0.5 ml PBS. To a 0.5 ml cell sample 0.5 ml RNAse (Type I-A, Sihma, St. Louis, Mo.) was added, followed after gentle mixing by 1 ml propidium iodide (PI, Sigma, 100 ug/ml in PBS) solution. The mixed cells were incubated in the dark at room temperature for 15 minutes and kept at 4° C. in the dark until measured.

(2) The second method was essentially that described in the protocol of APO-DIRECT. The 300×g centrifuged cell pellet was fixed in 4% cold paraformaldehyte in PBS for 15 minutes and washed in PBS, resuspended in 0.5 ml of PBS.

DNA fragmentation assay and DNA electrophoresis

C33A cells were incubated in the absence or presence of 500 uM DFMO for the indicated times. Adherent cells were collected after trypsin treatment and combined with cells collected from the growth medium. Cells were washed in PBS, pelleted (3 min, 500 g) and incubated overnight at 37° C. in lysis buffer (10 mM Tris/HCI, 10 mM EDTA, 0.5% Triton X-100, 50 ug/ml proteinase K, 5 u/ml Rnase A). DNA was extracted with equal volumes of phenol and chloroform/ 3-methylbutan-1-ol (24:1, v/v) and precipitated with 0.1 vol. of 3M sodium acetate, pH 5, and 2.5 vol. of cold 100% ethanol. Pelleted DNA was resuspended in TE (10 mM Tris/HCL, 1 mM EDTA) and was electrophoresed on a 1.5% agarose gel in TAE buffer (40 mM Tris/acetate, 1 mM EDTA. The gel was stained in 1 ug/ml ethidium bromide in TAE for 30 minutes, destained in TAE and photographed under UV illumination.

RNA purification and analysis by Northern Blotting

Total cellular RNA was purified by the method of TRI Reagen (Molecular Research Center, Inc.) RNA (20 ug per lane) was fractionated on a 1.2% (w/v) agarose/ formaldehyde gel and transferred to positively charged nylon filters (Amersham). The probes were labeled with 32P-dCTP to a specific activity of approximately $2 \times 10^9$ cpm/ug using the random hexanucleotides (Prime - It II- Kit, Stratagene, La Jolla, Calif.) as primers. The filters were pre-hybridized and hybridized at 65° C. in Rapid-Hyb Buffer (Amersham) for 15 minutes and overnight respectively and were washed twice with 2×SSC, 0.1% SDS at room temperature for 15 minutes. The final washes were done to a stringency of 0.1x SSC, 1% SDS at 65° C. for 15 minutes for 3 times. The membranes were then placed against an Hyper-film (Amersham) for autoradiography at 70° C. for 1–2 days using intensifying screens.

Figure 4:
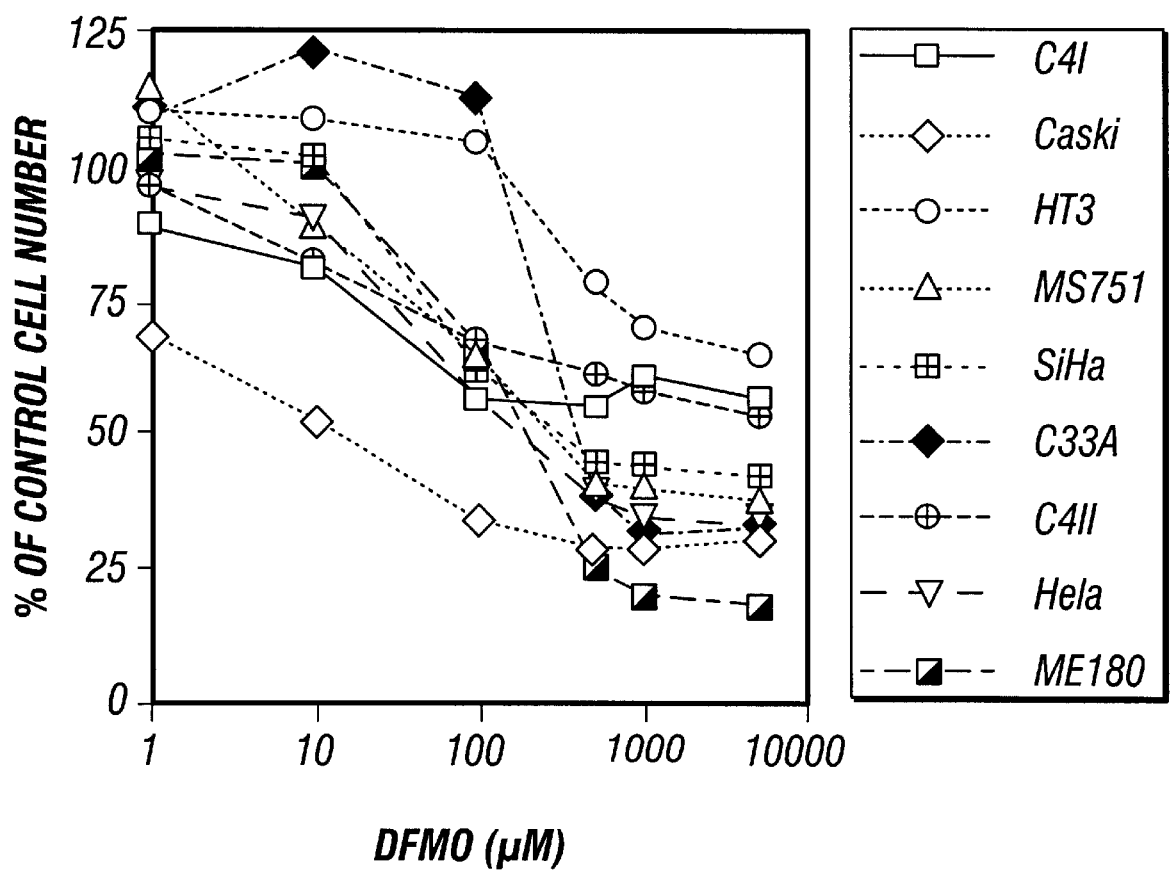
FIG. 4—Antiproliferative effects of DFMO of the indicated concentration on cells after continuous treatment for 5 days. Results are expressed as a percentage of the respective untreated controls. The points represent mean values of 8-duplicate cultures. The standard deviation did not exceed 5%.
Figure 5:
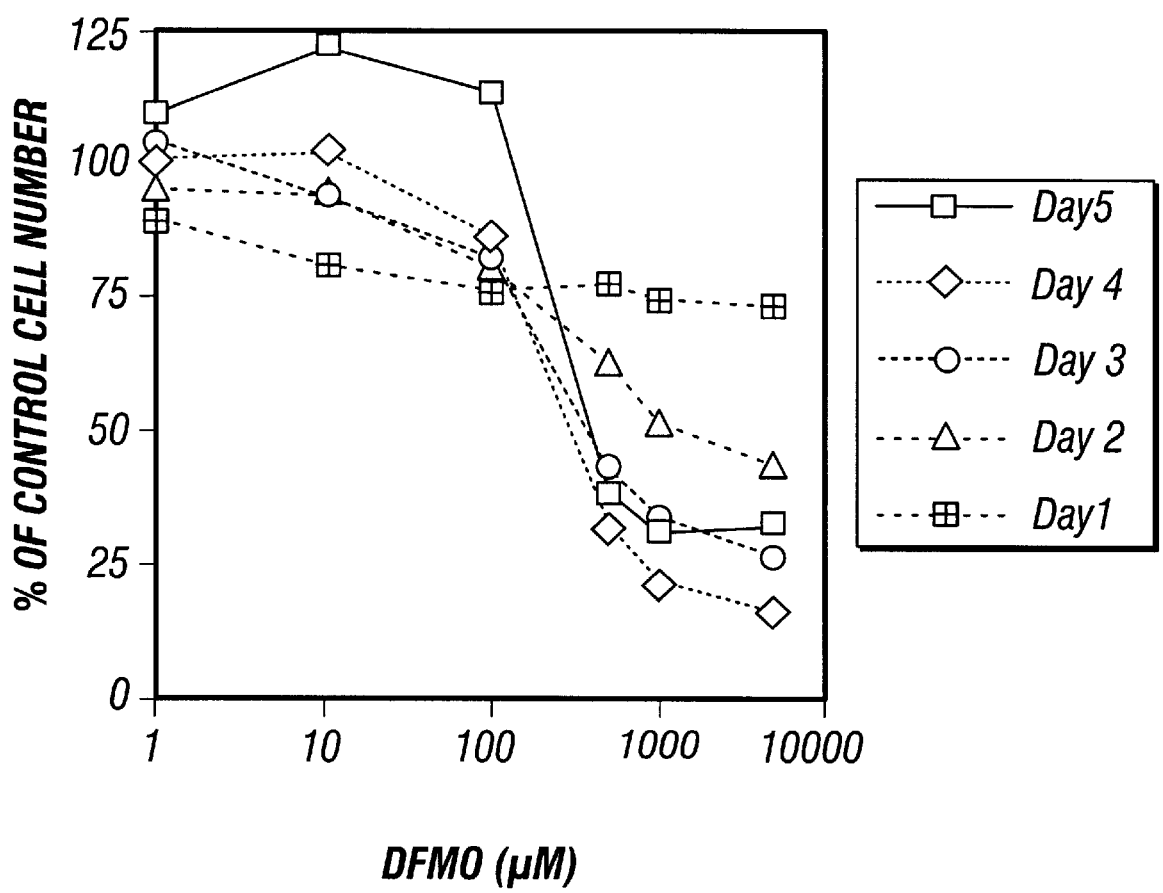
FIG. 5—Shows the effect of DFMO on the growth of C33A cells. C33A cells were incubated in the absence or presence of different concentrations of DFMO for the indicated times (1 $\mu$M, 10 $\mu$M, 100 $\mu$M, 500 $\mu$M, 1000 $\mu$M, 1400 $\mu$M DFMO).
Figure 6:
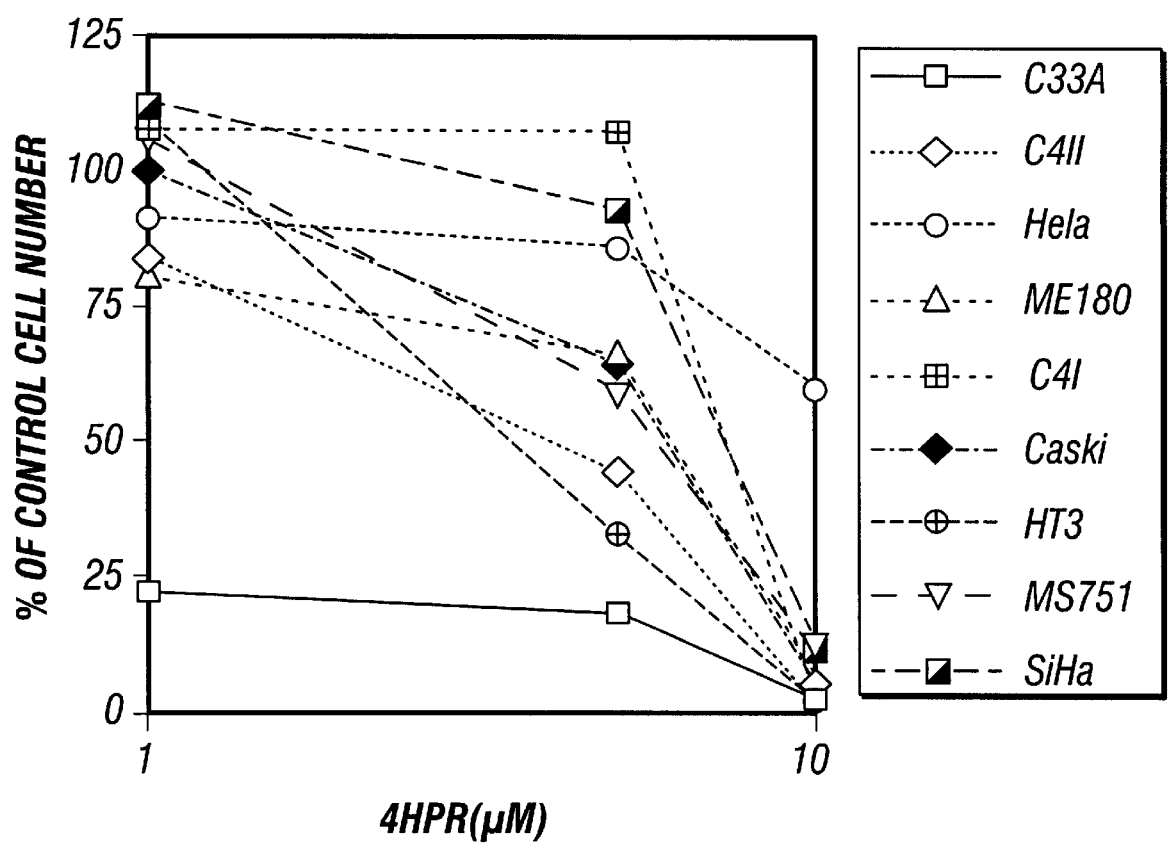
FIG. 6—Shows the growth inhibitory effects of 4-HPR on several different human cervical carcinoma cell lines. The concentrations of 4-HPR examined were 1 $\mu$M, 5 $\mu$M and 10 $\mu$M. (Graph legends: C33A line, —□—; C411 line, —◇—; Hela line, —○—; ME180 line, —△—; C41 line, —■—; Caski line, —◆—; HT3 line, —▼—; MS751 line —▽—; SiHa line, —▣—).

These results from these studies are shown in FIGS. 4, 5 and 6, and in Table 5, below.

TABLE 5

Effect of 4-HPR on the Growth of HCC Cell Lines

| Cells | (μM) | (μM) |
| --- | --- | --- |
| C33A | 300 | <1 |
| C-41 | 35 | 7 |
| C-411 | 400 | 5 |
| Caski | 15 | 5 |
| HeLa | 30 | Not measurable |
| HT3 | Not measurable | 3+ |
| Me180 | 300 | 6– |
| MS751 | 100 | 6– |
| SiHa | 45 | 7+ |

These data demonstrate that DFMO provides an inhibitory effect on the growth of a number of diverse human tumor cell lines, and the utility of the present invention as a method for inhibiting or treating cancer, and particularly cervical cancer and CIN in humans.

REFERENCES

The following references, to the extent that they provide exemplary procedural or other details supplementary to those set forth herein, are specifically incorporated herein by reference.

1. A REPORT FROM THE CDC ON FOUR STUDIES IN NEW YORK CITY. The risk for cervical disease in HIV-infected women. Primary Care & Cancer, 11:51–2, 1991.
2. ALDOUS S, ET AL. Resolution of (+)- and (-1-alpha- difluoromethylornithine by capillary gas chromatography. J. Chromatogr. (1986) 357 (2) 335–9.
3. ANSEL HC, POPOVICH NG AND ALLEN LV, JR., EDS. Pharmaceutical Dosage Forms and Drug Delivery Systems, 6th Ed. Williams & Wilkins, Baltimore, ISBN 0-683-00193-0, 1995.
4. AUVINEN M., PAASINEN A., ANDERSSON LC, HOLTTA E., Orinthine decarboxylase activity is critical for cell transformation. Nature 360:355–8, 1992.
5. BOONE C. W., KELLOFF G. J., MALONE W. E. Identification of candidate cancer chemopreventive agents and their evaluation in animal models and human clinical trials: a review. Cancer Res. 50:2–9, 1990.
6. BOSCH F. X., MANOS M. M., MUNOZ N,, ET AL. Prevalence of human papillomavirus in cervical cancer: A worldwide perspective. J Natl Cancer Inst 87:796–802, 1995.
7. CARBONE P. P., LOVE R. R., CAREY P., TUTSCH K., VERMA A. K., WILDING G, GILMORE-CUNNINGHAM D. Difluoromethylornithine (DFMO), a Potential Chemopreventive (Meeting Abstract). Proc. Annual Meet Am Assoc Cancer Res. Vol. 32, pp. A1209, 1991.
8. CREAVEN P. J., PENDYALA L., PORTER C. W., MURPHY, M. J. Alpha-Difluoromethylornithine (DFMO) as a Potential Chemopreventive Agent: Toxicology, Phannacokinetics and Pharmacodynamics of Chronic Oral Administration in Humans (Meeting abstract); Non-serial, (1993). CCPC-93: Second International Cancer Chemo Prevention Conference. Apr. 28–30, 1993, Berlin, Germany, p. 53.
9. CREAVEN P. J., PENDYALA L, PETRELLI N, DOUGLASS H, HERRERA L, PORTER C, SOLOMON J. Phase I Study of Difluoromethylornithine DFMO as a Chemopreventive Agent (CPA) (meeting abstract); Proc. Annual Meet Am. Soc. Clin. Oncol. Vol. 11, pp. A395, 1992.
10. CREAVEN P. J., PENDYALA L, PETRELLI NJ. Evaluation of α-difluoromethylornithine as a potential chemopreventive agent: Tolerance to daily oral administration in human. Cancer, Epidemiol, Biomarkers Prev. 2:243–7, 1993.
11. CROGHAN M. K., AICKIN MG, MEYSKENS FL JR. Dose-related α-difluoromethylornithine ototoxicity. Am. J. Clin. Oncol. 14:331–335, 1991.
12. CROWELL J. A., GOLDENTHAL EI, KELLOFF GJ, MALONE WF, BOONE. Chronic Toxicity Studies of the Potential Cancer Preventive 2-(difluoromethyl)-d,1-ornithine. CW Fundam Appl Toxicol, (1994) 22/3 (341–354).
13. DALY M. B. The chemoprevention of cancer: directions for the future. Cancer Epidemiol Biomarkers Prev. 2:509–12, 1993.
14. GOLDENTHAL EI. One Year Oral Toxicity Study of Difluoromethylornithine in Rats and in Dogs. International Research and Development Corporation, Reports 560-032 and 560-033, 1990.
15. GREENWALD P, MALONE WF, CERNY ME, STERN HR. Cancer Prevention Research Trials; Maryland 20892, U.S.A. 1993. Adv. Cancer Res. (1993) (61, 1–23, 1993) 5 FIG. 4 Tab. 74 Ref.
16. GRIFFIN C, ABELOFF MD, SLAVIK M, ET AL. Phase I trial and pharmacokinetic study of intravenous and high dose oral α-difluoromethylornithine (DFMO). Proc. ASCO 3:34, 1984.
17. GRIFFIN C. A., SLAVIK M, CHIEN SC, ET AL. Phase I trial and pharmacokinetic study of intravenous and oral α-difluoromethylornithine. Invest new Drugs 5:177–186, 1987.

18. HAEGELE K. D., ALKIN RG, ET AL. Kinetics of alpha-difluoromethylornithine: an Irreversible Inhibitor of Ornithine Decarboxylase. Clin. Phannacol. Ther. 30(2):210–17, 1981.
19. HARRIS W. B., GROSSIE V. B., OTA D. M, NISHIOKA K., ET AL. Effect of difluoromethylornithine on host and tumor polyamine metabolism during total parenteral nutrition. J. Surg. Res. 38:592–8, 1985.
20. HORN Y; SCHECHTER P J; MARTON L J. Phase I–II Clinical Trial with Alpha-Difluoromethylornithine—An Inhibitor of Polyamine Biosynthesis. Eur. J. Cancer Clin. Oncol. (23, No. 8, 1103–07, 1987) 7 Tab. 22 Ref.
21. IN VIVO EVALUATION OF A COLON-SPECIFIC DRUG DELIVERY SYSTEM: An Absorption Study of Theophylline from Capsules Coated with Azo Polymers in Rats. Pharmaceutical Res. 12(2):244–247, 1995.
22. KELLOFF GJ, BOONE CW, CROWELL JA, STEELE VE, LUBET R, DOODY LA. Surrogate endpoint biomarkers for phase II cancer chemoprevention trails. J Cell Biochem Suppl 19:1–9., 1994.
23. KELLOFF GJ, BOONE CW, CROWELL JA, STEELE VE, LUBET R, SIGMAN CC. Chemopreventive Drug Development: Perspectives and Progress. Bethesda, Md. CIDU, Natl. Cancer Inst. 85–98, 1994.
24. KURMAN R.J., HENSON DE, HERBST AL, ET AL. Interim guidelines for management of abnormal cervical cytology. The 1992 National Cancer Institute Workshop. JAMA 271:1866–9. 1994.
25. LIEBERMAN H. A., LACHMAN L and SCHWARTZ JB, EDS. Pharmaceutical Dosage Forms: Tablets, Vol. 3. Marcel Dekker, Inc., NY ISBN 0-8247-8300-X, 1990.
26. LOVE R. R., CARBONE PP, VERMA AK, GILMORE D, CAREY P, TUTSCH KD, POMPLUN M, WILDING G. Randomized phase I chemoprevention dose-seeking study of $\alpha$-difluoromethylornithine. J Natl Cancer Inst 85:732–6, 1993.
27. LUK G. D., ABELOFF MD, GRIFFIN CA, ET AL. Successful treatment with DL-alpha-difluoromethylornithine(DFMO) of established human small cell lung carcinoma implants in athymic mice. Proc. AACR 24:318, 1983.
28. MAMONT PS, DUCHESNE MC, GROVE J, ET AL. Antiproliferative properties of DL-alpha- difluoromethylornithine in cultured cells. A consequence of ornithine decarboxylase. Biochem. Biophys. Res. Commun. 81:58–66, 1978.
29. MARX M, TOWNSEND CM JR, BARRANCO SC, ET AL. Treatment of hamster pancreatic cancer with a-difluoromethylomithine, an inhibitor of polyamine biosynthesis. J. Natl. Cancer Inst. 79:543–548, 1987.
30. MCGINITY JW, ED. Aqueous Polymeric Coatings for Pharmaceutical Dosage Forms. Marcel Dekker, Inc., NY ISBN 0-8247-7907-X, 1989.
31. MEYSKENS FL, SURWIT EA, MOON TE, ET AL. Enhancement of regression of cervical intraepithelial neoplasia II (moderate dysplasia) with topically applied all-trans-retinoic acid: a randomized trail. J. Natl. Cancer Inst. 86:539–43, 1994.
32. MITCHELL MF, HITTELMAN WN HONG WK, ET AL. The natural history of cervical intraepithelial neoplasia: an argument for intermediate endpoint biomarkers. Cancer Epidemiol Biomarkers Prev. 3:619–26, 1994.
33. PARKIN DM, PISANI P, FERLAY J. Estimates of the worldwide incidence of eighteen major cancers in 1985. Int. J. Cancer 54:594–606. 1993.
34. PENDYALA L, CREAVEN PJ, PORTER CW. Urinary and erythrocyte polyamines during the evaluation of oral a-difluoromethylornithine in a phase I chemoprevention trail clinical trial. Cancer, Epidemiol, Biomarkers Prevention 2:235–41, 1993.
35. PRAKASH NJ, SCHECHTER PJ, MAMONT PS, ET AL. Inhibition of EMT 6 tumor growth by interference with polyamine biosynthesis; effects of alpha-difluoromethylornithine, an irreversible inhibitor of ornithine decarboxylase. Life Sci. 26:181–194, 1980.
36. ROBINSON JR and LEE V HL LEE, EDS. Controlled Drug Delivery: Fundamentals and Applications, 2nd ed. Marcel Dekker, Inc., NY ISBN 0-8247-7588-0, 1987.
37. SCHMITT-HOFFMANN AH, HAEGELE KD. Pharmacokinetics of the Enantiomers of $\alpha$-difluoromethylornithine. Annual Report of the CIFRE Convention, 1987.
38. SPORN MB. Chemoprevention of cancer. Lancet 342:1211–3, 1993.
39. STEELE V E; BOONE C W; KELLOFF G J. Use of agent combinations in the chemoprevention of experimental cancer. Proc.Am.Assoc.Cancer Res. (35, 85 Meet., 628, 1994).
40. TAKAM H, UMEMOTO S, ABE O, ET AL. Effects of alpha-difluoromethyl-ornithine (DFMO) combined with mitomycin C (MMC) in human tumors transplanted into nude mice. PROC. AACR 30:A2338, 1989.
41. TESTA B. Chiral Aspects of Drug Metabolism. TIPS, February 1986.
42. TOER TN. Colonic Drug Delivery. Proceed Intern. Symp. Control Rel. Bioact. Mater, Mar. 16 (1990), pg. 126–127, pg. 291–295.
43. VAN DEN MOOTER G, ET AL. The Relation Between Swelling Properties and Enzymatic Degradation of Azo Polymers Designed for Colon-Specific Drug Delivery. Pharmaceutical Res. 11(12):1737–1741, 1994.
44. VAN DEN MOOTER G, ET AL. Characterization of Colon-Specific Azopolymers: A Study of the Swelling Properties and the Permeability of Isolated Polymer Fiulms. Internat'l J. Pharmaceutics (1994), 111 pg. 127–136.
45. VANDELLI MA, ET AL. A Delayed Delivery System for the Colonic Drug Release; Proc. 1st World Mtg. APGI/APV, Budapest, 9/11, May 1995, pg. 278–279.
46. VERMA AK, BOUTWELL RK. Inhibition of carcinogenesis by inhibitors of putrescine biosynthesis. In: McCann PP, Pegg AE, Sjoerdsma A editors. Inhibition of polyamine metabolism, biological significance and basis for new therapies. Orlando, Fla.: Academic Press, 1987:249–58.
47. WAGNER, J. ET AL. Resolution of the enantiomers of various alpha-substituted ornithine and lysine analogs by high performance liquid chromatography with chiral eluent and by gas chromatography on chirasil-Val. Anal. Biochem. (1987), 164(1), 102–16. WILDING IR, ET AL. Enteric Coated Timed Release Systems for Colonic Targeting. Internat'l J. Pharmaceutics (1994), 111, pg. 99–102.

What is claimed is:

1. A method of inhibiting progression of cervical epithelial neoplasia to cervical cancer comprising administering to a patient in need thereof a pharmaceutical preparation comprising a pharmacologically active amount of DFMO, or pharmaceutically acceptable salts thereof, in a pharmaceutically acceptable carrier, thereby inhibiting progression of cervical epithelial neoplasia to cervical cancer.

2. A method of reducing the risk of cervical cancer in a patient with cervical epithelial neoplasia comprising administering to a patient having cervical epithelial neoplasia a pharmaceutical composition comprising a pharmacologically active amount of DFMO, or pharmaceutically acceptable salts thereof, in a pharmaceutically acceptable carrier.

3. A method of preventing premalignant tissue development in a patient in need thereof comprising administering to said patient a pharmaceutical preparation comprising a pharmacologically active amount of DFMO, or pharmaceutically acceptable salts thereof, in a pharmaceutically acceptable carrier, thereby preventing premalignant tissue development.

4. A method of inhibiting cervical intraepithelial neoplasia in a patient in need thereof comprising administering a pharmaceutical preparation comprising a pharmacologically active amount of DFMO, or pharmaceutically acceptable salts thereof, in a pharmaceutically acceptable carrier; thereby inhibiting cervical intraepithelial neoplasia.

5. The method of claim 1, 2, 3, or 4, wherein the pharmacologically active amount of DFMO is between about 0.01% to about 90% by weight of the pharmaceutical preparation.

6. The method of claims 1, 2, 3 or 4, wherein the patient is administered a dose of between about 0.050 $g/m^2$/day and about 10.0 $g/m^2$/day of DFMO.

7. The method of claim 4, wherein the cervical intraepithelial neoplasia is a cervical intraepithelial neoplasia grade I, II or III.

8. The method of claim 4, wherein the cervical intraepithelial neoplasia is a cervical intraepithelial neoplasia grade III.

9. The method of claims 1, 2, 3, or 4, wherein the method comprises treatment with a cytotoxic or cytostatic agent in addition to DFMO.

10. The method of claim 1, 2, 3, or 4, wherein DFMO is administered via an oral route.

11. The method of claim 1, 2, 3, or 4, wherein DFMO is administered via an intravenous route.

12. The method of claim 1, 2, 3, or 4, wherein said patient is infected with HPV.

13. The method of claim 1, 2, 3, or 4, wherein said patient is infected with HIV.

14. The method of claim 6, wherein the dose is between about 0.10 $g/m^2$/day and about 0.95 $g/m^2$/day of DFMO for about 30 days.

15. The method of claim 14, wherein the dose is between about 0.50 $g/m^2$/day and about 0.95 $g/m^2$/day of DFMO for about 30 days.

16. The method of claim 6, wherein the dose of DFMO is adjusted based on patient response or plasma levels DFMO.

17. The method of claim 6, wherein daily dosing with DFMO is continued for about 30 days.

18. The method of claims 1, 2, 3, or 4, wherein the DFMO is a racemic mixture of (D)- and (L)-DFMO.

19. The method of claims 1, 2, 3, or 4, wherein the DFMO is (L)-DFMO.

* * * * *

UNITED STATES PATENT AND TRADEMARK OFFICE
CERTIFICATE OF CORRECTION

PATENT NO. : 6,166,079
DATED : December 26, 2000
INVENTOR(S) : Follen et al.

Page 1 of 1

It is certified that error appears in the above-identified patent and that said Letters Patent is hereby corrected as shown below:

<u>Title page,</u>
Item [75], Inventors, please delete "Wuan K. Hong" and insert -- Waun K. Hong -- therefor.

Signed and Sealed this

Twelfth Day of February, 2002

Attest:

Attesting Officer

JAMES E. ROGAN
*Director of the United States Patent and Trademark Office*